US010253358B2

(12) United States Patent
Domanico et al.

(10) Patent No.: US 10,253,358 B2
(45) Date of Patent: Apr. 9, 2019

(54) MULTIPLE-CONTROL CALIBRATORS FOR DNA QUANTITATION

(71) Applicant: EXACT SCIENCES DEVELOPMENT COMPANY, LLC, Madison, WI (US)

(72) Inventors: Michael Domanico, Middleton, WI (US); Ilse A. Tyler, Poway, CA (US); Brian Aizenstein, Madison, WI (US); Hatim Allawi, Middleton, WI (US); Graham P. Lidgard, Middleton, WI (US)

(73) Assignee: EXACT SCIENCES DEVELOPMENT COMPANY, LLC, Madison, WI (US)

( * ) Notice: Subject to any disclaimer, the term of this patent is extended or adjusted under 35 U.S.C. 154(b) by 230 days.

(21) Appl. No.: 15/033,803

(22) PCT Filed: Nov. 4, 2014

(86) PCT No.: PCT/US2014/063875
§ 371 (c)(1),
(2) Date: May 2, 2016

(87) PCT Pub. No.: WO2015/066695
PCT Pub. Date: May 7, 2015

(65) Prior Publication Data
US 2016/0273030 A1    Sep. 22, 2016

Related U.S. Application Data

(60) Provisional application No. 61/899,302, filed on Nov. 4, 2013.

(51) Int. Cl.
*C12P 19/34*    (2006.01)
*C12Q 1/6851*    (2018.01)
*C12Q 1/6844*    (2018.01)

(52) U.S. Cl.
CPC ......... *C12Q 1/6851* (2013.01); *C12Q 1/6846* (2013.01)

(58) Field of Classification Search
CPC ............ C12Q 1/6846; C12Q 2521/301; C12Q 2525/204; C12Q 2545/113; C12Q 1/6851
USPC ...................................... 435/91.2; 536/320.1
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,352,775 A | 10/1994 | Albertsen et al. |
| 5,403,711 A | 4/1995 | Walder et al. |
| 5,409,818 A | 4/1995 | Davey et al. |
| 5,463,782 A | 11/1995 | Carlson et al. |
| 5,494,810 A | 2/1996 | Barany et al. |
| 5,508,169 A | 4/1996 | Deugau et al. |
| 5,527,676 A | 6/1996 | Vogelstein et al. |
| 5,624,802 A | 4/1997 | Urdea et al. |
| 5,639,611 A | 6/1997 | Wallace et al. |
| 5,648,212 A | 7/1997 | Albertsen et al. |
| 5,660,988 A | 8/1997 | Duck et al. |
| 5,670,325 A | 9/1997 | Lapidus et al. |
| 5,710,264 A | 1/1998 | Urdea et al. |
| 5,741,650 A | 4/1998 | Lapidus et al. |
| 5,773,258 A | 6/1998 | Birch et al. |
| 5,792,614 A | 8/1998 | Western et al. |
| 5,830,665 A | 11/1998 | Shuber et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,888,778 A | 3/1999 | Shuber |
| 5,914,230 A | 6/1999 | Liu et al. |
| 5,928,870 A | 7/1999 | Lapidus et al. |
| 5,952,178 A | 9/1999 | Lapidus et al. |
| 5,955,263 A | 9/1999 | Vogelstein et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,020,137 A | 2/2000 | Lapidus et al. |

(Continued)

FOREIGN PATENT DOCUMENTS

| | | |
|---|---|---|
| WO | WO 93/14224 | 7/1993 |
| WO | WO 02/070755 | 9/2002 |
| WO | WO 2005/023091 | 3/2005 |
| WO | WO 2008/084219 | 7/2008 |
| WO | WO 2013/142545 | 9/2013 |
| WO | WO 2015/066695 | 5/2015 |

OTHER PUBLICATIONS

Moskalev et al., Nucleic Acids Reserch, vol. 39, No. 11, e77, 1-12, Apr. 2011.*
Lin et al., PLoS ONE, vol. 6, iss. 12, e29101, pp. 1-10, Dec. 2011.*
Allawi et al., Invader plus method detects herpes simplex virus in cerebrospinal fluid and simultaneously differentiates types 1 and 2, J Clin Microbiol. Sep. 2006;44(9):3443-7.
Ballabio, et al., "Screening for steroid sulfatase (STS) gene deletions by multiplex DNA amplification," Human Genetics, 1990, 84(6): 571-573.
Barnay, "Genetic disease detection and DNA amplification using cloned thermostable ligase," Proc. Natl. Acad. Sci USA, 1991, 88:189-93.

(Continued)

*Primary Examiner* — Cynthia B Wilder
(74) *Attorney, Agent, or Firm* — Casimir Jones, S.C.; Mary Ann D. Brow

(57) ABSTRACT

The present invention provides DNA plasmids that find use as calibrators or reference standards for calculating DNA quantities in a sample. In particular, provided herein are DNA plasmids that contain multiple control fragments, and methods of their use in DNA quantitation.

8 Claims, 9 Drawing Sheets

Specification includes a Sequence Listing.

(56) References Cited

U.S. PATENT DOCUMENTS

| | | | |
|---|---|---|---|
| RE36,713 E | 5/2000 | Vogelstein et al. |
| 6,063,573 A | 5/2000 | Kayyem |
| 6,090,543 A | 7/2000 | Prudent et al. |
| 6,090,566 A | 7/2000 | Vogelstein et al. |
| 6,110,677 A | 8/2000 | Western et al. |
| 6,110,684 A | 8/2000 | Kemper et al. |
| 6,121,001 A | 9/2000 | Western et al. |
| 6,143,529 A | 11/2000 | Lapidus et al. |
| 6,146,828 A | 11/2000 | Lapidus et al. |
| 6,150,097 A | 11/2000 | Tyagi et al. |
| 6,183,960 B1 | 2/2001 | Lizardi |
| 6,203,993 B1 | 3/2001 | Shuber et al. |
| 6,210,884 B1 | 4/2001 | Lizardi |
| 6,221,583 B1 | 4/2001 | Kayyem et al. |
| 6,235,502 B1 | 5/2001 | Weissman et al. |
| 6,245,515 B1 | 6/2001 | Vogelstein et al. |
| 6,248,229 B1 | 6/2001 | Meade |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 6,351,857 B2 | 3/2002 | Slaon, III et al. |
| 6,406,857 B1 | 6/2002 | Shuber et al. |
| 6,415,455 B1 | 7/2002 | Slaon, III et al. |
| 6,428,964 B1 | 8/2002 | Shuber |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,551,777 B1 | 4/2003 | Shuber et al. |
| 6,586,177 B1 | 7/2003 | Shuber |
| 6,677,312 B1 | 1/2004 | Vogelstein et al. |
| 6,750,020 B2 | 6/2004 | Shuber |
| 6,800,617 B1 | 10/2004 | Vogelstein et al. |
| 6,812,339 B1 | 11/2004 | Venter et al. |
| 6,818,404 B2 | 11/2004 | Shuber |
| 6,844,155 B2 | 1/2005 | Shuber |
| 6,849,403 B1 | 2/2005 | Shuber |
| 6,872,816 B1 | 3/2005 | Hall et al. |
| 6,919,174 B1 | 7/2005 | Shuber |
| 6,964,846 B1 | 11/2005 | Shuber |
| 7,005,266 B2 | 2/2006 | Sprenger-Haussels |
| 7,087,583 B2 | 8/2006 | Vogelstein et al. |
| 7,267,955 B2 | 9/2007 | Vogelstein et al. |
| 7,368,233 B2 | 5/2008 | Shuber et al. |
| 7,432,050 B2 | 10/2008 | Markowitz |
| 7,485,420 B2 | 2/2009 | Markowitz |
| 7,662,594 B2 | 2/2010 | Kong et al. |
| 7,981,612 B2 | 7/2011 | Shuber et al. |
| 8,361,720 B2 | 1/2013 | Oldham-Haltom et al. |
| 8,715,937 B2 | 5/2014 | Zou et al. |
| 8,916,344 B2 | 12/2014 | Zou et al. |
| 2004/0241658 A1 | 12/2004 | Barrett et al. |
| 2007/0202525 A1 | 8/2007 | Quake et al. |
| 2009/0226976 A1 | 9/2009 | Reed |
| 2009/0253142 A1 | 10/2009 | Allawi et al. |
| 2012/0196756 A1 | 8/2012 | Ahlquist et al. |
| 2012/0288868 A1 | 11/2012 | Bruinsma et al. |
| 2013/0143216 A1 | 6/2013 | Oldham-Haltom et al. |
| 2013/0231256 A1 | 9/2013 | Oldham-Haltom et al. |

OTHER PUBLICATIONS

Barrett et al., Genetic Tools for Allelic Replacement in *Burkholderia* Species, Appl Environ Microbiol, 2008, 74:4498-4508.
Bustin, "Absolute quantification of mRNA using real-time reverse transcription polymerase chain reaction assays," J. Molecular Endocrinology, 2000, 25:169-193.
Ceska et al., Structure-specific DNA cleavage by 5' nucleases, Trends Biochem Sci. Sep. 1998;23(9):331-6.
Chamberlain et al., "Deletion screening of the Duchenne muscular dystrophy locus via multiplex DNA amplification," Nucleic Acids Research, 1988, 16(23):11141-11156.
Coll et al., Evaluation of a rapid method of extracting DNA from stool samples for use in hybridization assays, J Clin Microbiol. Oct. 1989;27(10):2245-8.
Don et al., "'Touchdown' PCR to circumvent spurious priming during gene amplification," Nucleic Acids Research, 1991, 19(14):4008.
GenBank Accession No. EU277853, 2008, 2 pages.
Guilfoyle et al., "Ligation-mediated PCR amplification of specific fragments from a class-II restriction endonuclease total digest," Nucleic Acids Research, 1997, 25:1854-1858.
Hall et al., "Sensitive detection of DNA polymorphisms by the serial invasive signal amplification reaction," PNAS, 2000, 97:8272.
Hayden et al., "Multiplex-Ready PCR: A new method for multiplexed SSR and SNP genotyping," BMC Genomics, 2008, 9:80.
Hecker et al., "High and low annealing temperatures increase both specificity and yield in touchdown and stepdown PCR," Biotechniques, 1996, 20(3):478-485.
Herman et al., "Methylation-specific PCR: a novel PCR assay for methylation status of CpG islands," PNAS, 1996, 93(13):9821-9826.
Higuchi et al., "A general method of in vitro preparation and specific mutagenesis of DNA fragments: study of protein and DNA interactions," Nucleic Acids Research, 1988, 16(15):7351-7367.
Higuchi et al., "Kinetic PCR analysis: real-time monitoring of DNA amplification reactions," Biotechnology, 1993, 11:1026-1030.
Higuchi et al., "Simultaneous amplification and detection of specific DNA sequences," Biotechnology, 1992, 10:413-417.
Kaiser M.W., et al., "A comparison of eubacterial and archaeal structure-specific 5'-exonucleases," (1999) J. Biol. Chem., 274:21387.
Kalinina et al., "Nanoliter scale PCR with TaqMan detection," Nucleic Acids Research, 1997, 25:1999-2004.
Lage et al, Whole genome analysis of genetic alterations in small DNA samples using hyperbranched strand displacement amplification and array-CGH, Genome Res. Feb. 2003;13(2):294-307.
Liu et al ., Flap endonuclease 1: a central component of DNA metabolism, Annu Rev Biochem. 2004;73:589-615.
Zou et al., Quantification of methylated markers with a multiplex methylation-specific technology, Clin Chem. Feb. 2012;58(2):375-8.
Lyamichev et al., "Polymorphism identification and quantitative detection of genomic DNA by invasive cleavage of oligonucleotide probes," Nat. Biotech., 1999, 17:292-296.
NEBuffer Activity/Performance Chart with Restriction Enzymes, New England Bio Labs, retrieved Mar. 13, 2015, www.neb.com/tools-and-resources/usage-guidelines/nebuffer-performance-chart-with-restriction-enzymes?device=pdf, 16 pages.
Nollau et al., Isolation of DNA from stool and bodily fluids for PCR amplification, Biotechniques. May 1996;20(5):784-8.
Olivier, The Invader assay for SNP genotyping, Mutat Res. Jun. 3, 2005;573(1-2):103-10.
Orpana, Fluorescence resonance energy transfer (FRET) using ssDNA binding fluorescent dye, Biomol Eng. Apr. 2004;21(2):45-50.
Roux, "Using mismatched primer-template pairs in touchdown PCR," Biotechniques, 1994, 16(5):812-814.
Ryan et al., Non-PCR-dependent detection of the factor V Leiden mutation from genomic DNA using a homogeneous invader microtiter plate assay., Mol Diagn. Jun. 1999;4(2):135-44.
Schouten et al., "Relative quantification of 40 nucleic acid sequences by multiplex ligation-dependent probe amplification," Nucleic Acids Research, 2002, 30(12): e57.
Selvin, Fluorescence resonance energy transfer, 1995, Methods Enzymol. 1995;246:300-34.
Sidransky et al., Identification of ras oncogene mutations in the stool of patients with curable colorectal tumors., Science. Apr. 3, 1992;256(5053):102-5.
Stryer, Fluorescence energy transfer as a spectroscopic ruler, Annu Rev Biochem. 1978;47:819-46.
Triglia et al., "A procedure for in vitro amplification of DNA segments that lie outside the boundaries of known sequences," Nucleic Acids Res., 1988, 16:8186.
Villa et al., Identification of subjects at risk for colorectal carcinoma through a test based on K-ras determination in the stool, Gastroenterology. May 1996;110(5):1346-53.
Vogelstein et al., "Digital PCR," PNAS, 1999, 96: 9236-41.

(56) References Cited

OTHER PUBLICATIONS

International Search Report and Written Opinion for PCT/US2014/063875, dated Apr. 1, 2015, 17 pages.

* cited by examiner

FIG. 1

SEQ ID NO: 1

AATACCGGATCAGGCGCCATTCGCCATTCAGGCTGCGCAACTGTTGGGAAGGGCGATCGGTGCGGGCCTCTTCGCTA
TTACGCCAGCTGGGCGAAAGGGCGATTGCTGCAAGGCGATTAAGTTGGGTAACGCCAAGGTTTTCCCAGTCACGACG
TTGTAAAACGACGGCCAGTGAATTCGAGCTCGGTACCTCGCGAATGCATCTAGATGATGAATTCTTGGAGTTTAATT
TTCGGTTTCGTCGTTTTTGCGTTTTTGGGGTATTTAGTCGCGTAGAAGGCGGAAGTGTGTGTAGGTATTAATATTGGTTTGTGATAAG
TTTGGTGTTTGTTTTTTTGATTAGGTGTTTAAGATAGTGTTTGGGTGTGTAGGTATTAATATTGGTTTGTGATAAG
GTTATGAGGTTGGTGTAAAGAATTCATCATCGGATCCCGGGCCCGTCGACTGCAGAGGCCTGCATGCAAGCTTGGC
GTAATCATGGTCATAGCTGTTTCCTGTGTGAAATTGTTATCCGCTAATGAGTGAGCTAACTCACATTAATT

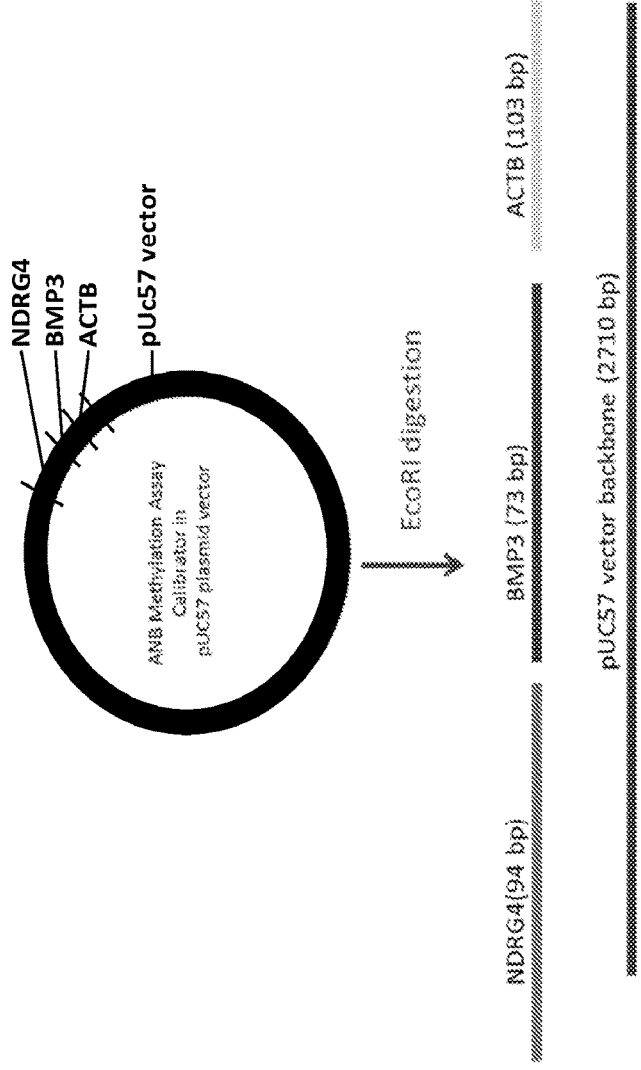

FIG. 2

SEQ ID NO: 6

AATACCCGCCATCAGGCGCGCCATTCGCCAATCTGTTGGGAAGGGCGATCGTCGTGCCGGGCCTCTTCGCTA
TTACGCCAGCTGGCGAAAGGGGGATGTGCTGCAAGGCGATTAAGTTGGGTAACGCCAGGGTTTTCCCAGTCACGACG
TTGTAAAACGACGGCCAGTGAATTCGAGCTCGGTACCTCGCGAATGCATCTAGATGAATTCACATTTTCATTATTTT
TATTATAAGGCCTGCTGCTGAAAATGACTGAATATAAACTTGTGGTAGTTGGAGCTGGTGGCGTAGGCAAGAGTGCCTTG
ACGATACAGACGCTAATTCAGAATCATTTTGTGGACGAATATGATCCAACAATAGAGGTAAATGAATTCACATTTTCAT
TATTTTTATTATAAGGCCTAATTCAGAATCATTTTGTGAAAATGACTGAATATAAACTTGTGGTAGTTGGAGCTGGTGGCGTAGGCAAGAGT
GCCTTGACGATACAGCTAATTCAGAATCATTTTGTGACAAGGCCATGAGGCCGTGTAAAGCGGCCTTGCATGCAAGCTTGGCGTAATCATGGTCATAGCTGTTCCTGTGAAATTGTTATCCGCTCACAATTCCACACATACGAGCCGGAAGCATAAAG
TGTAAAG

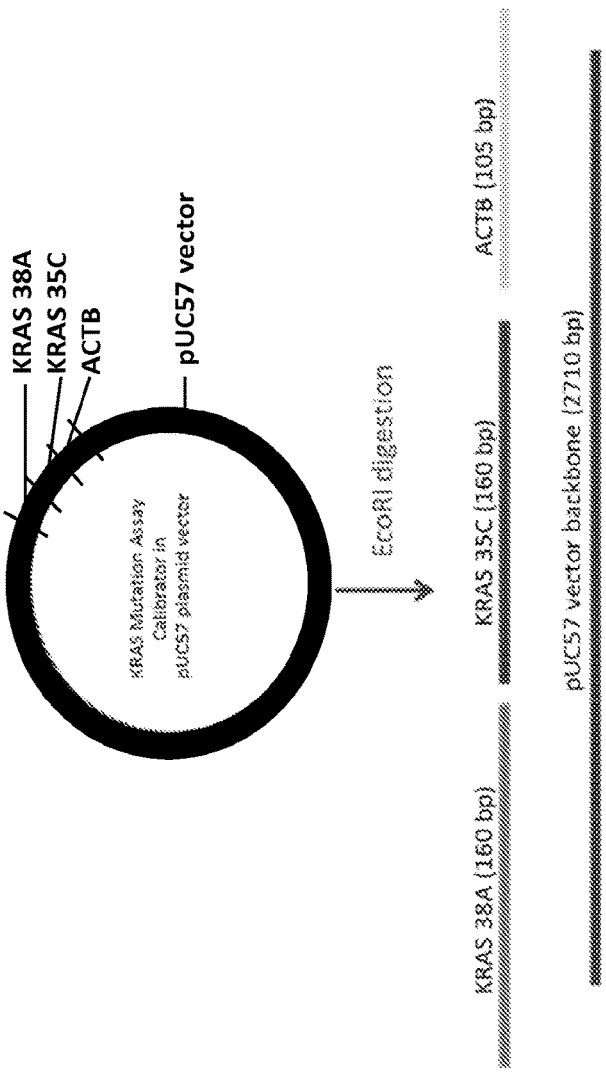

FIG. 3
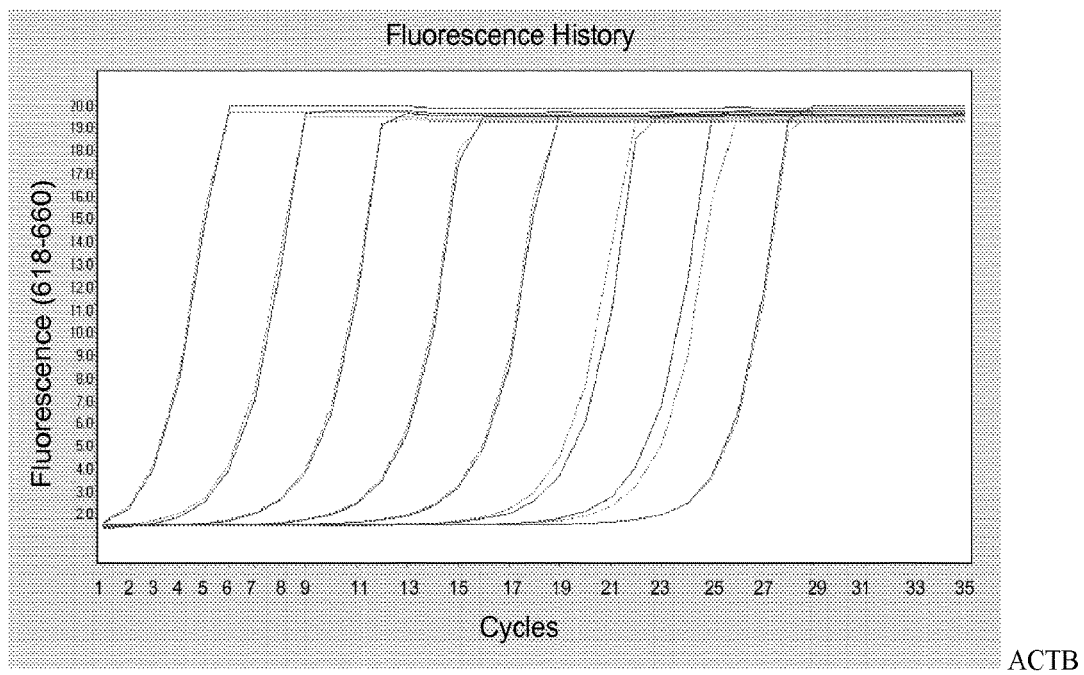
ACTB
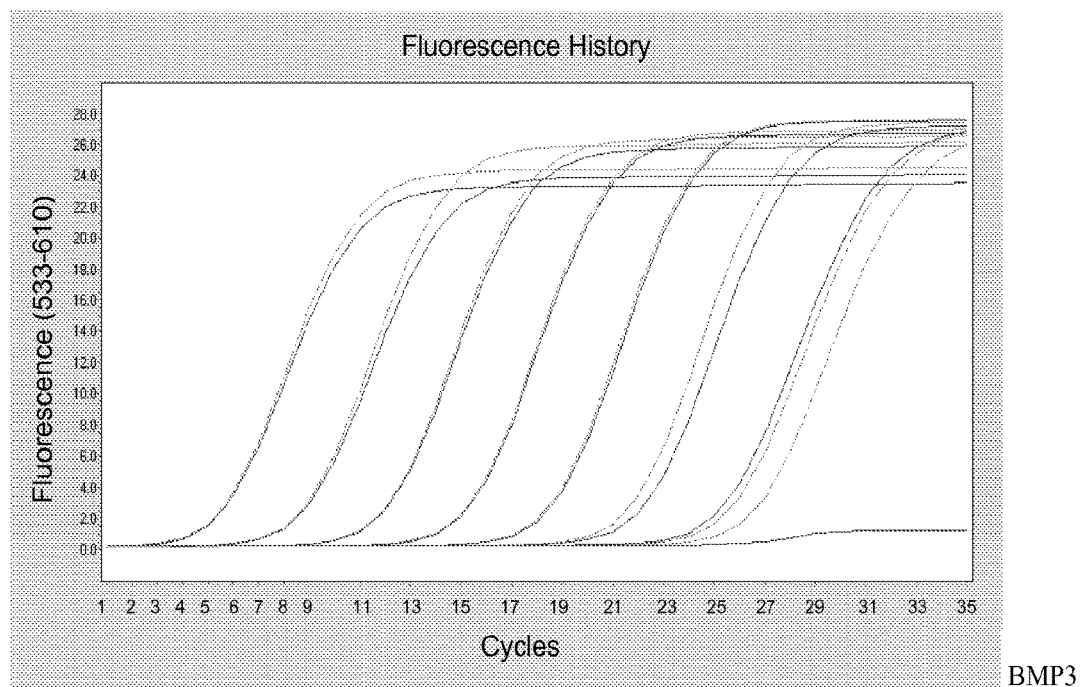
BMP3

FIG. 3 (con't)
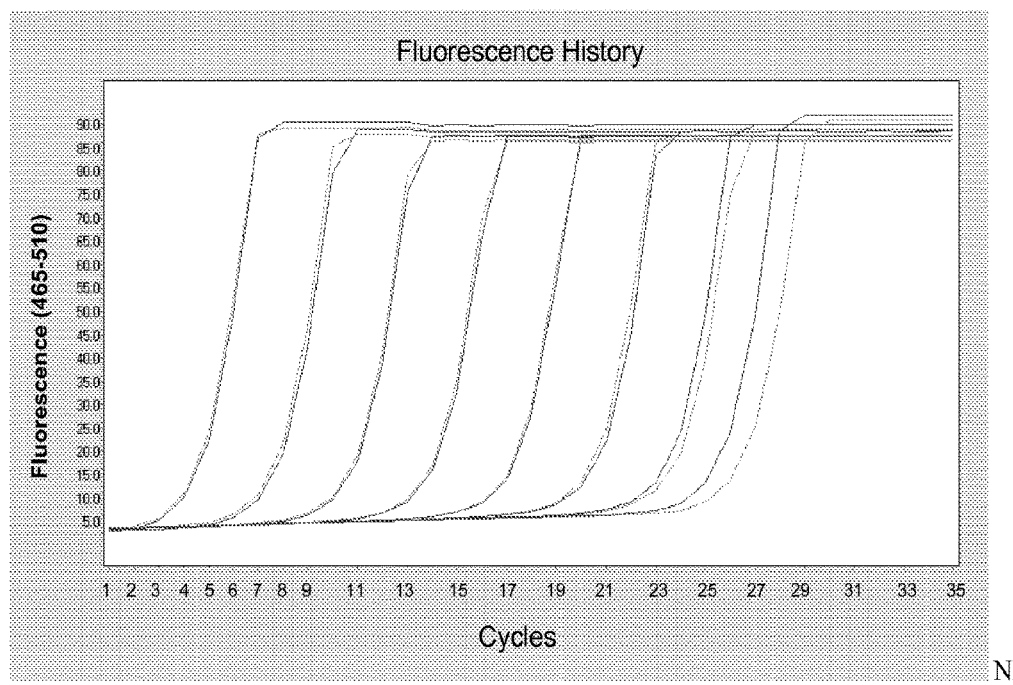
NDRG4

FIG. 4
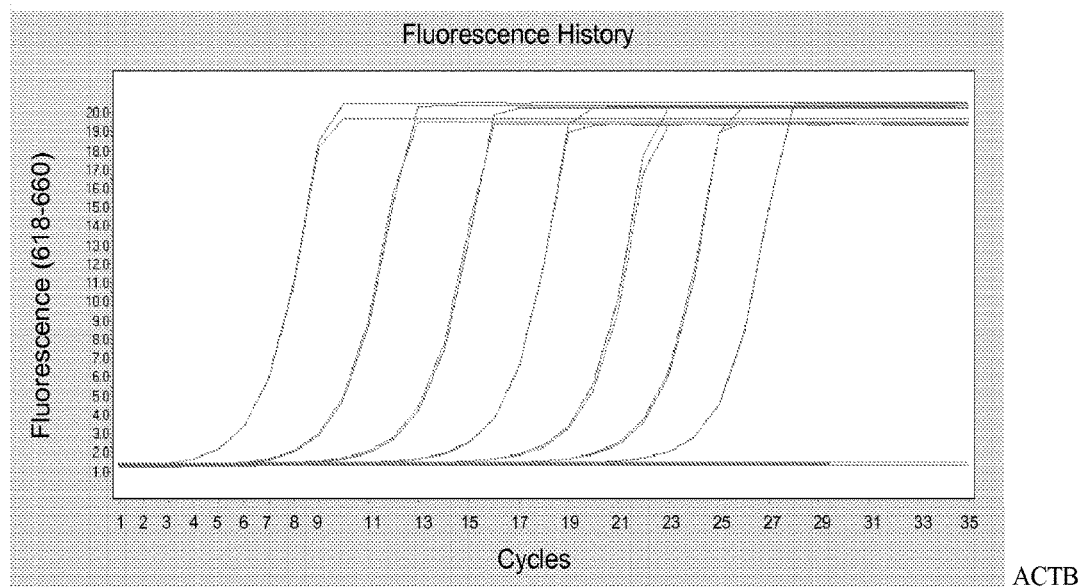
ACTB
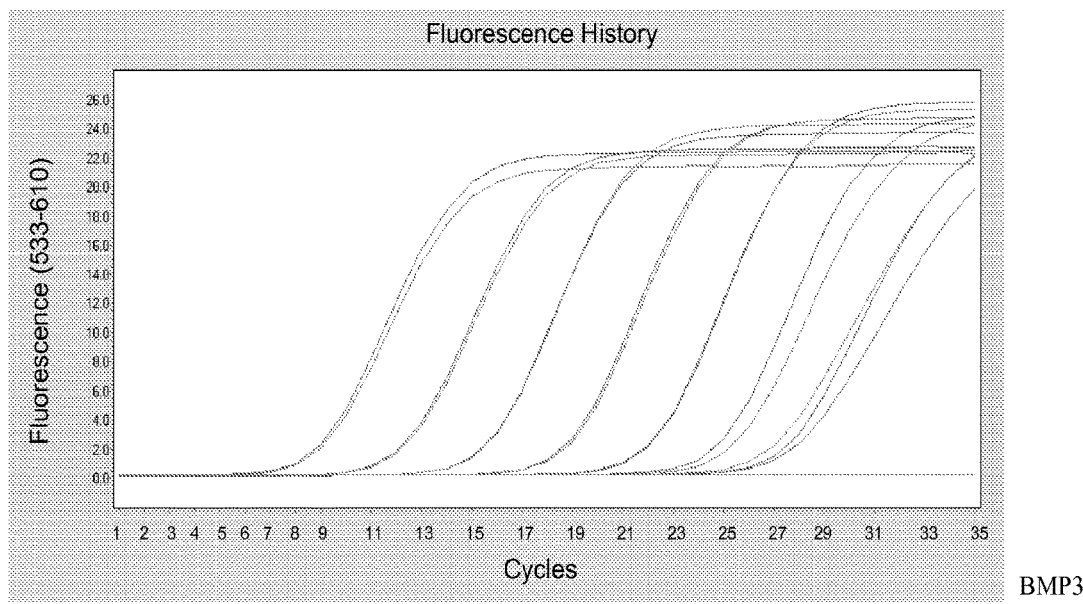
BMP3

FIG. 4 (con't)
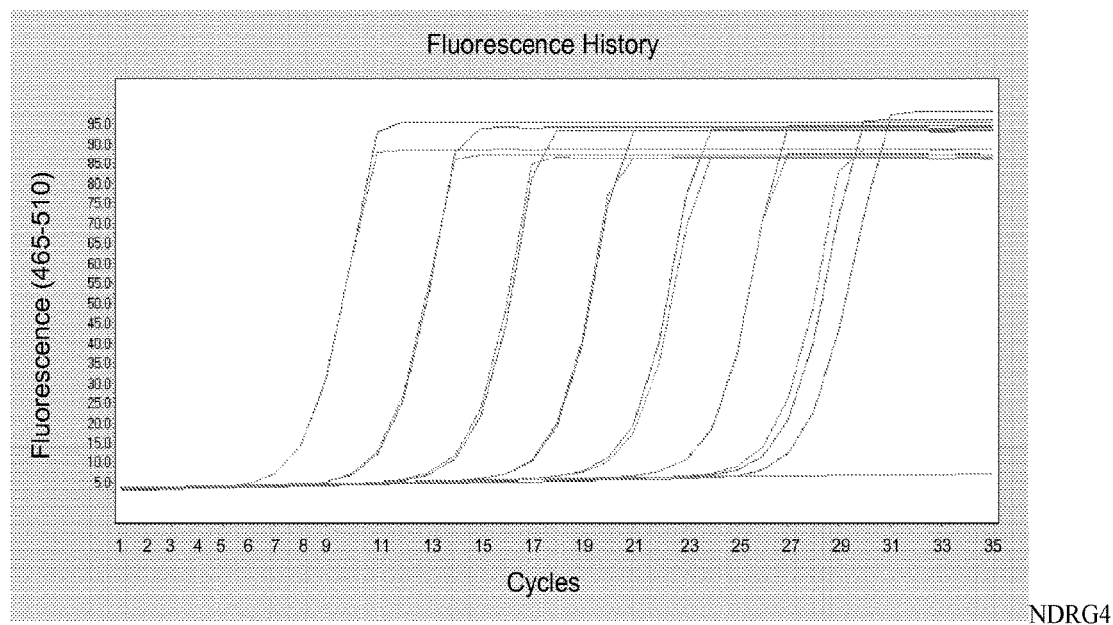
NDRG4

FIG. 6A

| SEQ ID NUMBER | Description | | LENGTH |
|---|---|---|---|
| SEQ ID NO:1 | Me Assay Calibrator Plasmid Portion (Fig. 1) | AATACCGCATCAGGCGCCATTCGCCATTCAGGCTGCGCAACTGTTGGGAAGGGCGA TCGGTGCGGGCCTCTTCGTCTATTACGCCAGCTGGCGAAAGGGGATGTGCTGCAAG GCGATTAAGTTGGGTAACGCCAGGGTTTCCCAGTCACGACGTTGTAAAACGACGG CCAGTGAATTCGAGCTCGGTACCTCGCGAATGCATCTAGATGCATGCATCTTGGAGT TTAATTTTCGGTTTCGTCGTCGGGTTTTCGTTTTCGTTTTCGGAGTGTTTCGTAGCGACGTCT TGAATTCTTCGTCGCGGTTTACGCGCGAGGGATCGCGTTGAATTCTTGGTGTTTGTTT CGTAGAAGGCGGAAGTTACGCGCGAGGGATCGCGTTGAATTCTTGGTGTTTGTTT TTTGATTAGGTGTTAAGATAGTGTTGTGGGTGTAGGTATTAATATTGGTTTGTGTG ATAAGGTTATGAGGTTGGTGTAAGAAGGAATTCATCATCGGATCCCGGCCCGTCGAC TGCAGAGGCCGTCATGCAAGCTGGCTAATCATGCATCATCGTCATAGCTGTTCCTGTGTGA AATTGTTATCCGCTCACAATTCCACACAACATACGAGCCGGAAGCATAAAGTGTAAA GCCTGGGGTGCCTAATGAGTGAGCTAACTCACATTAATT | 666 |
| SEQ ID NO:2 | Me Assay Calibrator Control Portion (all inserts) | GAATTCTTGGAGTTTAATTTTCGGTTTCGTCGTCGGTTTTTGCGTTTTCGGAGTGTT CGTAGCGACGTCTTGAATTCTTCGTCGCGGTTTTCGTCGTTTTCGTTCGTTTATCG GGTATTTTAGTCGCGTAGAAGGCGGAAGTTACGCGCGAGGGATCGCGTTGAATTCT TTGGTGTTTGTTTTTTGATTAGGTGTTAAGATAGTGTTGTGGGTGTAGGTATTAAT ATTGGTTTGTGTGATAAGGTTATGAGGTTGGTGTAAAGGAATTC | 276 |
| SEQ ID NO:3 | Me Assay Calibrator ACTB Portion | AATTCTTTGGTGTTTGTTTTTTGATTAGGTGTTAAGATAGTGTTGTGGGTGTAGGT ATTAATATTGGTTTGTGTGATAAGGTTATGAGGTTGGTGTAAAGG | 103 |
| SEQ ID NO:4 | Me Assay Calibrator NRDG4 Portion | AATTCTTGGAGTTTAATTTTCGGTTTCGTCGTCGGTTTTTGCGTTTTCGGAGTGTTTC GTAGCGACGTCTTG | 73 |
| SEQ ID NO:5 | Me Assay Calibrator BMP3 Portion | AATTCTTCGTCGCGGTTTTCGTCGTTTTCGTTCGTTTATCGGGTATTTTAGTCGCG TAGAAGGCGGAAGTTACGCGCGAGGGATCGCGGTTG | 94 |

FIG. 6B

| SEQ ID NUMBER | Description | | LENGTH |
|---|---|---|---|
| SEQ ID NO:6 | Mutation Assay Calibrator Plasmid Portion (Fig. 2) | AATACCGCATCAGGCGCCATTCGCCATTCAGGCTGCGCAACTGTTGGGAAGGGCGA<br>TCGGTCGCGGGCCTCTTCGCTATTACGCCAGCTGCGCGGCGAAAGGGGGATGTGCTGCAAG<br>GCGATTAAGTTGGGTAACGCCAGGGTTTTCCCAGTCACGACGTTGTAAAACGACGG<br>CCAGTGAATTCGAGCTCGGTACCTCGCGAATGCATCTAGATGATCACATTTTCAT<br>ATTTTATTATAAGGCCTGCTGAAAATGACTGAATATAAACTTGTGGTAGTTGGAGC<br>TGGTGACGTAGGCAAGAGTGCCTTGACGATACAGCTAATTCACATTTCAGAATCATTTTGTGGA<br>CGAATATGATCCAACAATAGAGGTAAATCAACTTGTGGTAGTTGGAGCTGCTGGCGTAG<br>AGGGCCTGCTGAAAATGACTGATACAGCTAATATAAACTTGTGGTAGTTGGAGCTGCTGGCGTAG<br>GCAAGAGTGCCTTGACGATACAGCTAATTCTTGTGGGTGTAGGTACTAACACTGGCTCGTGTG<br>CAACAATAGAGGTAAATCGAATTCTTGTGGGTGTAGGTACTAACACTGGCTCGTGTG<br>ACAAGGCCATGAGCTGTGTAAAGCGGCCTTGGAGTGTGTATTAAGTAGGTGCAC<br>AGTAGGTCTGGAATTCATCGGATCCGGCCCGTGCAGAGGCCTGCATGCA<br>AGCTTGGCGTAATCATGGTCATAGCTGTTTCCTGTGTGAAATTGTTATCCGCTCACAA<br>TTCCACACAACATACGAGCCGGAAGCATAAAGTGTAAAG | 777 |
| SEQ ID NO:7 | Mutation Assay Control Portion (all inserts) | GAATTCACATTTCATTATTTTATTATAAGGCCTGCTGAAAATGACTGAATATAAAC<br>TTGTGGTAGTTGGAGCTGGTGACGTAGGCAAGAGTGCCTTGACGATACAGCTAATT<br>CAGAATCATTTTGTGGACGAATATGATCCAACAATAGAGGTAAATCGAATTCACATT<br>TTCATTATTTTTATTATAAGGCCTGCTGAAAATGACTGAATATAAACTTGTGGTAGTT<br>GGAGCTGCTGGCGTAGGCAAGAGTGCCTTGACGATACAGCTAATTCAGAATCATTTT<br>GTGGACGAATATGATCCAACAATAGAGGTAAATCGAATTCTTGTGGGTGTAGGTAC<br>TAACACTGGCTCGTGTGACAAGGCCATGAGCTGTGGTGTACAGCGGCCTTGGAGTGT<br>GTATTAAGTAGGTGCACAGTAGGTCTGGAATTC | 431 |
| SEQ ID NO:8 | Mutation Assay Calibrator KRAS 38A Portion | AATTCACATTTCATTATTTTATTATAAGGCCTGCTGAAAATGACTGAATATAAACT<br>TGTGGTAGTTGGAGCTGGTGACGTAGGCAAGAGTGCCTTGACGATACAGCTAATTC<br>AGAATCATTTTGTGGACGAATATGATCCAACAATAGAGGTAAATCG | 160 |
| SEQ ID NO:9 | Mutation Assay Calibrator KRAS 35C Portion | AATTCACATTTCATTATTTTATTATAAGGCCTGCTGAAAATGACTGAATATAAACT<br>TGTGGTAGTTGGAGCTGCTGGCGTAGGCAAGAGTGCCTTGACGATACAGCTAATTC<br>AGAATCATTTTGTGGACGAATATGATCCAACAATAGAGGTAAATCG | 160 |
| SEQ ID NO:10 | Mutation Assay Calibrator ACTB Portion | AATTCTTGTGGGTGTAGGTACTAACACTGGCTCGTGTGACAAGGCCATGAGGCTGG<br>TGTAAAGCGGCCTTGGAGTGTGTATTAAGTAGGTGCACAGTAGGTCTGG | 105 |

```
                        SEQUENCE LISTING

<160> NUMBER OF SEQ ID NOS: 10

<210> SEQ ID NO 1
<211> LENGTH: 666
<212> TYPE: DNA
<213> ORGANISM: Homo sapiens

<400> SEQUENCE: 1
aataccgcat caggcgccat tcgccattca ggctgcgcaa ctgttgggaa gggcgatcgg     60
tgcgggcctc ttcgctatta cgccagctgg cgaaaggggg atgtgctgca aggcgattaa    120
gttgggtaac gccagggttt tcccagtcac gacgttgtaa aacgacggcc agtgaattcg    180
agctcggtac ctcgcgaatg catctagatg atgaattctt ggagtttaat tttcggtttc    240
gtcgtcggtt ttttgcgttt tcggagtgtt tcgtagcgac gtcttgaatt cttcgtcgcg    300
gttttcgttc gttttttcgt tcgtttatcg ggtattttag tcgcgtagaa ggcggaagtt    360
acgcgcgagg gatcgcgttg aattctttgg tgtttgtttt tttgattagg tgtttaagat    420
agtgttgtgg gtgtaggtat taatattggt ttgtgtgata aggttatgag gttggtgtaa    480
aggaattcat catcggatcc cgggcccgtc gactgcagag gcctgcatgc aagcttggcg    540
taatcatggt catagctgtt tcctgtgtga aattgttatc cgctcacaat tccacacaac    600
atacgagccg gaagcataaa gtgtaaagcc tggggtgcct aatgagtgag ctaactcaca    660
ttaatt                                                               666

<210> SEQ ID NO 2
<211> LENGTH: 276
<212> TYPE: DNA
<213> ORGANISM: Homo sapiens

<400> SEQUENCE: 2
gaattcttgg agtttaattt tcggtttcgt cgtcggtttt ttgcgttttc ggagtgtttc     60
gtagcgacgt cttgaattct tcgtcgcggt tttcgttcgt ttttcgttc gtttatcggg    120 tattttagtc gcgtagaagg cggaagttac gcgcgaggga tcgcgttgaa ttctttggtg    180
tttgtttttt tgattaggtg tttaagatag tgttgtggg gtaggtatta atattggttt    240
gtgtgataag gttatgaggt tggtgtaaag gaattc                              276

<210> SEQ ID NO 3
<211> LENGTH: 103
<212> TYPE: DNA
<213> ORGANISM: Homo sapiens

<400> SEQUENCE: 3
aattctttgg tgtttgtttt tttgattagg tgtttaagat agtgttgtgg gtgtaggtat     60
taatattggt ttgtgtgata aggttatgag gttggtgtaa agg                      103

<210> SEQ ID NO 4
<211> LENGTH: 73
<212> TYPE: DNA
<213> ORGANISM: Homo sapiens

<400> SEQUENCE: 4
```

```
aattcttgga gtttaattتt cggtttcgtc gtcggttttt tgcgttttcg gagtgtttcg    60
tagcgacgtc ttg                                                       73
```

<210> SEQ ID NO 5
<211> LENGTH: 94
<212> TYPE: DNA
<213> ORGANISM: Homo sapiens

<400> SEQUENCE: 5

```
aattcttcgt cgcggttttc gttcgttttt tcgttcgttt atcgggtatt ttagtcgcgt    60
agaaggcgga agttacgcgc gagggatcgc gttg                                94
```

<210> SEQ ID NO 6
<211> LENGTH: 777
<212> TYPE: DNA
<213> ORGANISM: Homo sapiens

<400> SEQUENCE: 6

```
aataccgcat caggcgccat tcgccattca ggctgcgcaa ctgttgggaa gggcgatcgg    60
tgcgggcctc ttcgctatta cgccagctgg cgaaaggggg atgtgctgca aggcgattaa   120
gttgggtaac gccagggttt tcccagtcac gacgttgtaa aacgacggcc agtgaattcg   180
agctcggtac ctcgcgaatg catctagatg aattcacatt ttcattatttttattataag    240 gcctgctgaa aatgactgaa tataaacttg tggtagttgg agctggtgac gtaggcaaga   300
gtgccttgac gatacagcta attcagaatc attttgtgga cgaatatgat ccaacaatag   360
aggtaaatcg aattcacatt ttcattattt ttattataag gcctgctgaa aatgactgaa   420
tataaacttg tggtagttgg agctgctggc gtaggcaaga gtgccttgac gatacagcta   480
attcagaatc attttgtgga cgaatatgat ccaacaatag aggtaaatcg aattcttgtg   540
ggtgtaggta ctaacactgg ctcgtgtgac aaggccatga ggctggtgta aagcggcctt   600
ggagtgtgta ttaagtaggt gcacagtagg tctggaattc atcggatccc gggcccgtcg   660
actgcagagg cctgcatgca agcttggcgt aatcatggtc atagctgttt cctgtgtgaa   720
attgttatcc gctcacaatt ccacacaaca tacgagccgg aagcataaag tgtaaag      777
```

<210> SEQ ID NO 7
<211> LENGTH: 431
<212> TYPE: DNA
<213> ORGANISM: Homo sapiens

<400> SEQUENCE: 7

```
gaattcacat tttcattatt tttattataa ggcctgctga aaatgactga atataaactt    60
gtggtagttg gagctggtga cgtaggcaag agtgccttga cgatacagct aattcagaat   120
cattttgtgg acgaatatga tccaacaata gaggtaaatc gaattcacat tttcattatt   180
tttattataa ggcctgctga aaatgactga atataaactt gtggtagttg gagctgctgg   240
cgtaggcaag agtgccttga cgatacagct aattcagaat cattttgtgg acgaatatga   300
tccaacaata gaggtaaatc gaattcttgt gggtgtaggt actaacactg gctcgtgtga   360
caaggccatg aggctggtgt aaagcggcct tggagtgtgt attaagtagg tgcacagtag   420
gtctggaatt c                                                       431
```

<210> SEQ ID NO 8
<211> LENGTH: 160
<212> TYPE: DNA

```
<213> ORGANISM: Homo sapiens

<400> SEQUENCE: 8
aattcacatt ttcattattt ttattataag gcctgctgaa aatgactgaa tataaacttg      60
tggtagttgg agctggtgac gtaggcaaga gtgccttgac gatacagcta attcagaatc     120
attttgtgga cgaatatgat ccaacaatag aggtaaatcg                           160

<210> SEQ ID NO 9
<211> LENGTH: 160
<212> TYPE: DNA
<213> ORGANISM: Homo sapiens

<400> SEQUENCE: 9
aattcacatt ttcattattt ttattataag gcctgctgaa aatgactgaa tataaacttg      60
tggtagttgg agctgctggc gtaggcaaga gtgccttgac gatacagcta attcagaatc     120
attttgtgga cgaatatgat ccaacaatag aggtaaatcg                           160

<210> SEQ ID NO 10
<211> LENGTH: 105
<212> TYPE: DNA
<213> ORGANISM: Homo sapiens

<400> SEQUENCE: 10
aattcttgtg ggtgtaggta ctaacactgg ctcgtgtgac aaggccatga ggctggtgta      60
aagcggcctt ggagtgtgta ttaagtaggt gcacagtagg tctgg                    105
```

US 10,253,358 B2

MULTIPLE-CONTROL CALIBRATORS FOR DNA QUANTITATION

The present application claims priority to U.S. Provisional Application Ser. No. 61/899,302, filed Nov. 4, 2013, which is incorporated herein by reference.

FIELD

The present invention provides DNA plasmids that find use as calibrators or reference standards for calculating DNA quantities in a sample. In particular, provided herein are DNA plasmids that contain multiple control fragments, and methods for their use in DNA quantitation.

BACKGROUND

For quantitative nucleic acid amplification, plasmids that contain copies of the target sequence(s) are routinely used as reference standards to generate calibration curves. Typically, a calibration curve is generated for each amplification target. A serial dilution of a known concentration of the calibrator nucleic acid is prepared, each diluted sample is subjected to PCR (or another amplified detection method), and the accumulation of product is monitored by detection of a signal (e.g., fluorescence) that accumulates in proportion to the amount of amplified target. The curve of accumulated signal from the amplified calibrator can then be used to determine the amount of the same target DNA in an unknown sample, i.e., by comparing the signal from the calibrators to the signal accumulated during amplification of the unknown. The amount of the target in the unknown sample can be calculated by comparison to the calibration data. See, e.g., Higuchi R, Fockler C, Dollinger G, Watson R, "Kinetic PCR Analysis: Real-time Monitoring of DNA Amplification Reactions", *Bio-Technology* 11: 1026-1030 (1993).

Standard curve production becomes problematic when a multiplex detection format is used, i.e., when several targets are amplified in the same reaction. For such samples, generation of the calibration data requires use of different target nucleic acids that are provided in a mixture in precise, known ratios, e.g., mixtures in which there are the same number of copies of each of the different target nucleic acids. Producing such refined control mixtures can be problematic, however. For example, routine inaccuracies in the methods for measuring concentrations of different preparations of nucleic acid, e.g., due to co-purifying non-target nucleic acids, proteins, diverse extinction coefficients, and/or other solutes that influence instruments used to measure nucleic acids concentration, make it difficult to produce different target nucleic acid preparations that are precisely matched in concentration. The same inaccuracies make it difficult to reliably combine different nucleic acids to produce mixtures at known molar ratios, e.g., in equal molar amounts, for use as calibrators for multiplexed quantitative amplification reactions.

In addition the inaccuracies in concentration, the configurations and conformations of different target nucleic acids can affect the efficiency of amplification. For example, the same target sequence may produce slightly different quantitative amplification results depending on whether the target sequence is in a supercoiled plasmid, in large genomic DNA, or in short, fragmented DNA.

SUMMARY

The present invention provides calibrator DNAs that find use as reference standards for calculating DNA quantities in a sample. In particular, provided herein are calibrator DNA, e.g., plasmids, that contain multiple control fragments. The present invention further provides methods of using the calibrator DNAs to produce equimolar mixtures of different control fragments representing target nucleic acids, on linear DNA fragments.

In some embodiments, the present invention provides a calibrator DNA comprising: (a) a vector portion, and (b) a control portion; wherein the control portion comprises two or more serially-linked control fragments separated by restriction endonuclease recognition sites, wherein the vector portion circularizes the calibrator DNA by flanking both ends of the control portion, and wherein the vector portion and the control portion are separated by restriction endonuclease recognition sites. In some embodiments, the restriction endonuclease recognition sites that separate (i) the vector portion from the control portion, and (ii) the serially-linked control fragments from each other are enzymatically cleavable under the same reaction conditions. In some embodiments, the restriction endonuclease recognition sites that separate: (i) the vector portion from the control portion, and (ii) the serially-linked control fragments from each other, are recognitions sites for the same endonuclease. In some embodiments, the control portion is between 50 and 2000 nucleotides in length. In some embodiments, the control portion is between 200 and 600 nucleotides in length. In some embodiments, each control fragment is between 10 and 500 nucleotides in length. In some embodiments, each control fragment is between 50 and 200 nucleotides in length. In some embodiments, the control portion comprises three control fragments. In some embodiments, the control fragments comprise portions of the human ACTB, NDRG4, and BMP3 genes. In some embodiments, one control fragment comprises a portion of the human ACTB gene. In certain embodiments, the calibrator DNA fragments comprise modifications to mimic bisulfite-converted DNA fragments. For example, in some embodiments, the control fragments comprise portions of the human ACTB, NDRG4, and BMP3 genes wherein residues that are non-methylated C residues in the natural target DNA are replaced with T residues, and wherein residues that are methylated C residues in the natural target DNA are replaced with C residues.

In some embodiments, one control fragment comprises at least 70% sequence identity to SEQ ID NO:3. In some embodiments, one control fragment comprises at least 10 contiguous nucleotides of SEQ ID NO:3. In some embodiments, one control fragment comprises a portion of the human NDRG4 gene. In some embodiments, one control fragment comprises at least 70% sequence identity to SEQ ID NO:4. In some embodiments, one control fragment comprises at least 10 contiguous nucleotides of SEQ ID NO:4. In some embodiments, one control fragment comprises a portion of the human ACTB gene. In some embodiments, one control fragment comprises at least 70% sequence identity to SEQ ID NO:5. In some embodiments, one control fragment comprises at least 10 contiguous nucleotides of SEQ ID NO:5. In some embodiments, the control portion comprises at least 70% sequence identity to SEQ ID NO:2. In some embodiments, a plasmid is provided having at least 70% sequence identity to SEQ ID NO:1. In some embodiments, one or more of the control fragments comprise a portion of the human KRAS gene. In some embodiments, one control fragment comprises a portion of the human KRAS gene having a 38A mutation. In some embodiments, one control fragment comprises at least 70% sequence identity to SEQ ID NO:8. In some embodiments, one control fragment comprises at least 10 contiguous nucleotides of SEQ ID NO:8. In some embodiments, one control fragment comprises a portion of the human KRAS gene having a 35C mutation. In some embodiments, one control fragment comprises at least 70% sequence identity to SEQ ID NO:9. In some embodiments, one control fragment comprises at least 10 contiguous nucleotides of SEQ ID NO:9. In some embodiments, one control fragment comprises a portion of the ACTB gene. In some embodiments, one control fragment comprises at least 70% sequence identity to SEQ ID NO:10. In some embodiments, one control fragment comprises at least 10 contiguous nucleotides of SEQ ID NO:10. In some embodiments, the control portion comprises at least 70% sequence identity to SEQ ID NO:7. In some embodiments, a plasmid is provided having at least 70% sequence identity to SEQ ID NO:6.

In some embodiments, the present invention provides reaction mixtures comprising calibrator DNAs (e.g., control plasmids) described herein, or fragments thereof (e.g., restriction fragments of the control portion). In some embodiments, a reaction mixture further comprises one or more of: DNA polymerase (e.g., a thermostable polymerase), deoxynucleoside triphosphates, amplification buffer, primer oligonucleotides, probe oligonucleotide, and magnesium salt. In some embodiments, reaction mixtures further comprise reagents for an invasive cleavage assay. In some embodiments, reagents for an invasive cleavage assay comprise flap assay reagent. In some embodiments, the flap assay reagents comprise one or more reagents selected from the list consisting of an invasive oligonucleotide, a flap oligonucleotide, a flap endonuclease, and a FRET cassette. In some embodiments, reaction mixtures further comprise appropriate endonuclease(s) for the restriction endonuclease recognition sites of the plasmid.

In some embodiments, the present invention provides assay systems comprising: (a) a first reaction mixture comprising a reaction mixture described herein; and (b) a second reaction mixture comprising separate target polynucleotides comprising sequences that are identical or complimentary to all or a portion of each of the control fragments in the first reaction mixture. In some embodiments, the first and second reaction mixtures are in separate vessels. In some embodiments, the separate vessels are wells in a single microwell plate. In some embodiments, the separate vessels are separate microcentrifuge tubes. In some embodiments, assay systems further comprise one or more additional reaction mixtures comprising separate target polynucleotides comprising sequences that are identical or complimentary to all or a portion of each of the control fragments. In some embodiments, the reaction mixtures further comprise one or more of DNA polymerase, deoxynucleoside triphosphates, amplification buffer, primer oligonucleotides, probe oligonucleotide, and magnesium salt. In some embodiments, the reaction mixtures further comprise reagents for an invasive cleavage assay. In some embodiments, the reagents for an invasive cleavage assay comprise flap assay reagent. In some embodiments, flap assay reagents comprise one or more reagents selected from the list consisting of an invasive oligonucleotide, a flap oligonucleotide, a flap endonuclease, and a FRET cassette. In some embodiments, the reaction mixtures further comprise one or more restriction endonucleases capable of cleaving DNA at the restriction endonuclease recognition sites present in the calibrator DNA. In some embodiments, target polynucleotides are isolated from stool. In some embodiments, target polynucleotides are each independently all or a portion of a polynucleotide fragment of 500 nucleotides or less. In some embodiments, target polynucleotides are each independently all or a portion of a polynucleotide fragment of 200 nucleotides or less. In some embodiments, target polynucleotides are each independently all or a portion of a polynucleotide fragment of 100 nucleotides or less.

In some embodiments, the present invention provides methods of quantitating two or more nucleic acid amplification reactions performed in a single vessel comprising: (a) providing: (i) a first vessel comprising a known initial quantity of a calibrator DNA and/or a calibrator mixture described herein and reagents for performing nucleic acid amplification of the control fragments, and (ii) a second vessel comprising an unknown initial quantity of two or more target sequences and reagents for performing a nucleic acid amplification reaction; (b) exposing said vessels to appropriate conditions for nucleic acid amplification to produce amplicons; (c) quantifying a signal from the amplicons in the first vessel and the second vessel; (d) quantifying the amplification of the two or more target sequences based on: (i) the signal from the amplicons in the first vessel and the second vessel, and (ii) the known starting quantity of the plasmid. In some embodiments, the method further comprise a step prior to step (b) of exposing the reaction mixture of the first vessel to restriction endonuclease capable of cleaving DNA at the restriction endonuclease recognition sites present in the calibrator DNA. In some embodiments, the signal from the amplicons is detected by an invasive cleavage assay. In some embodiments, the invasive cleavage assay is a flap assay. In some embodiments, flap assay reagents comprising one or more reagents selected from the list consisting of an invasive oligonucleotide, a flap oligonucleotide, a flap endonuclease, and a FRET cassette are added to the first and second vessels. In some embodiments, the first vessel and the second vessel are separate wells in a single microwell plate. In some embodiments, the first vessel and the second vessel are separate microcentrifuge tubes.

In some embodiments, the present invention provides methods comprising: (a) isolating nucleic acid from a biological or environmental sample; (b) amplifying the control fragments from a known initial quantity of a calibrator DNA and/or a calibrator mixture in a first vessel to produce control amplicons from control fragments in the calibrator; (c) simultaneously amplifying target sequences from the isolated nucleic acid that are identical or complimentary to all or a portion of each of the control fragments to produce target amplicons; (d) detecting a signal from the control amplicons and the target amplicons; (e) quantifying the amplification of the target sequences based on: (i) the signal from the control amplicons and target amplicons, and (ii) the known initial quantity of the plasmid. In some embodiments, the biological or environmental sample is a stool sample. In some embodiments, the stool sample is from a human subject. In some embodiments, methods further comprise the initial steps of the human subject collecting the stool sample and delivering it to a testing facility where one or more of steps (a)-(e) are performed. In some embodiments, delivering is by mailing or shipping. In some embodiments, the isolated nucleic acid is in fragments. In some embodiments, the fragments are less than 500 nucleotides in length. In some embodiments, the fragments are less than 200 nucleotides in length. In some embodiments, the fragments are less than 100 nucleotides in length. In some embodiments, the control fragments and the target sequences are in separate vessels during one or more (e.g., all) of steps (b)-(e). In some embodiments, the calibrator DNA is exposed, prior to step (b), one or more restriction endonucleases capable of cleaving DNA at the restriction endonuclease recognition sites of a calibrator DNA to produce separated control fragments. In some embodiments, the amplifying of steps (b) and (c) are by PCR (e.g., qPCR). In some embodiments, the signal from the amplicons is detected by an invasive cleavage assay. In some embodiments, the invasive cleavage assay is flap assay. In some embodiments, flap assay reagents comprising one or more reagents selected from the list consisting of an invasive oligonucleotide, a flap oligonucleotide, a flap endonuclease, and a FRET cassette are present or added for the detecting step.

BRIEF DESCRIPTION OF THE DRAWINGS

FIG. 1 shows the design of a methylation assay calibrator plasmid ("ANB"). The pUC57 plasmid vector contains three methylation assay target sequences (shaded in grey) separated by EcoRI restriction sites (shaded in black). The ACTB (reference gene beta actin), NDRG4, and BMP3 sequences present in this construct represent the bisulfite-converted versions of these targets.

FIG. 2 shows the design of a mutation assay calibrator plasmid ("KRAS"). The pUC 57 plasmid vector contains all three mutation assay target sequences: KRAS 38A, KRAS 35C and ACTB (reference gene beta actin), shaded in grey, separated by EcoRI restriction sites shaded in black.

FIG. 3 shows graphs demonstrating equivalency of single and double purification protocols for the ANB triplex calibrator plasmid. Serial dilutions of 32233F (single purification anion exchange) vs. 32233G (double purification, anion exchange and hydrophobic interaction) from 1E7 to 1E0 copies/reaction are shown.

FIG. 4 shows graphs demonstrating the accuracy of $A_{260}$ quantitation post anion exchange purification. A midi-scale prep of the ANB triplex calibrator plasmid was purified over a Qiagen Tip20 anion exchange column, quantified by $A_{260}$ and serially diluted alongside the previously quantified and Poisson validated calibrator 32233F. The superimposition of the curves shows that anion exchange purification allows accurate quantification of the resulting preparation of DNA.

FIGS. 6A-6B provide a table showing SEQ ID NOS:1-10.

DEFINITIONS

Figure 5:
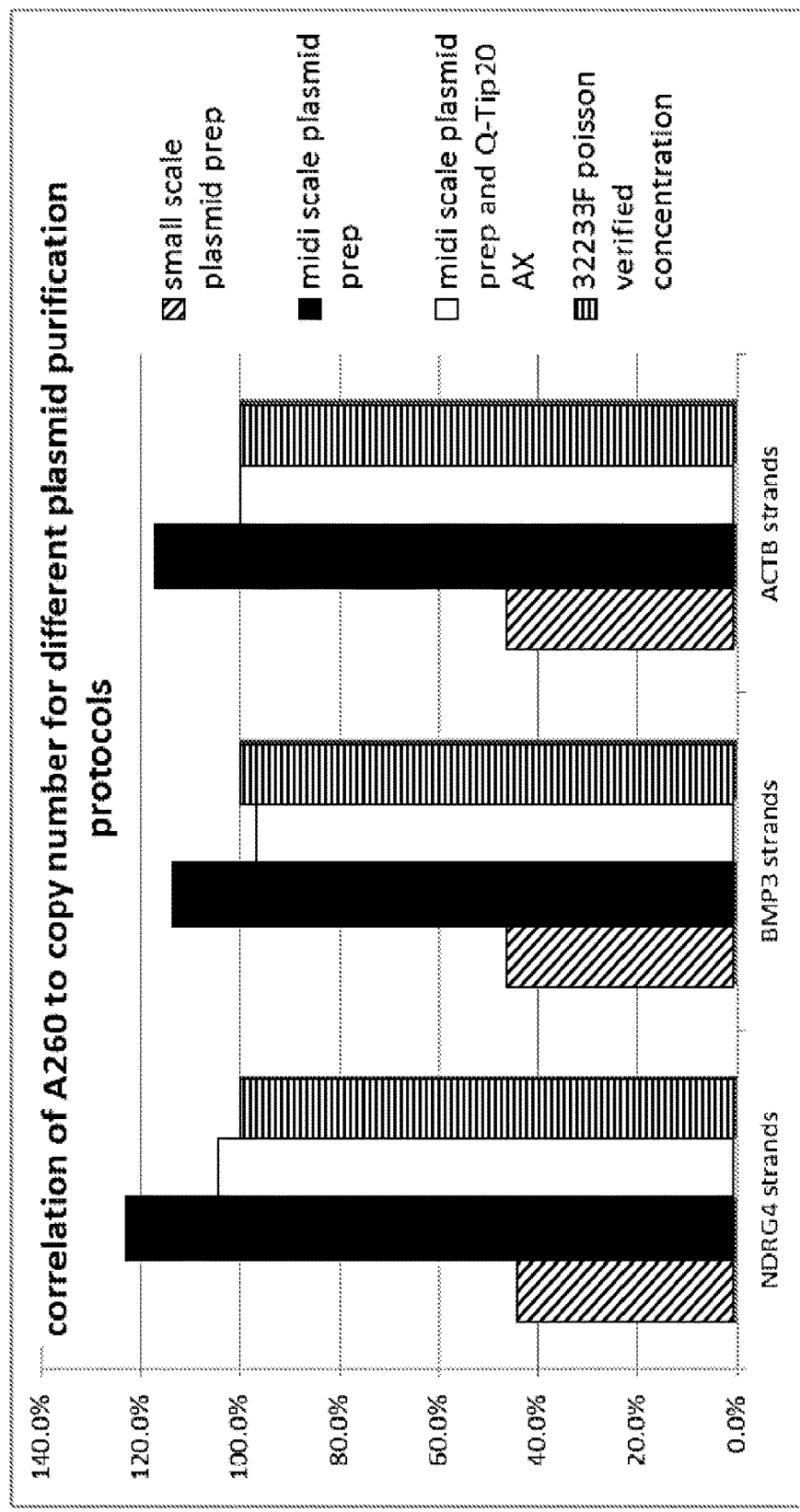
FIG. 5 shows a graph depicting improved correlation between $A_{260}$ and Poisson sampling with inclusion of an anion exchange column step in the plasmid purification procedure.

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "analyte" is to be construed broadly as any compound, molecule, element, ion, or other substance of interest to be detected, identified, or characterized.

As used herein, the terms "subject" and "patient" refer to an animal, preferably a human, from which a stool specimen is collected. In some instances, the subject is also a "user" (and thus the user is also the subject or patient).

The term "sample" as used herein is used in its broadest sense. For example, a sample relates to a material or mixture of materials, typically, although not necessarily, in liquid form, containing one or more analytes of interest. A sample may be obtained from a biological, environmental, or synthetic source. In particular embodiments, a sample is suspected of containing a human gene or chromosome or sequences (e.g., fragments) associated with a human chromosome. Samples may comprise a cell, chromosomes isolated from a cell (e.g., a spread of metaphase chromosomes), genomic DNA (e.g., in solution or bound to a solid support), RNA (e.g., in solution or bound to a solid support), cDNA (e.g., in solution or bound to a solid support) and the like. A sample may contain contaminants (e.g., non-target nucleic acid, proteins, small molecules, biological or environmental matter, etc.) or may be in a purified or semi-purified form.

The terms "target" and "target sequence" when used in reference to a nucleic acid detection or analysis method herein, refers to a nucleic acid having a particular sequence of nucleotides to be detected or analyzed, e.g., in a sample or reaction mixture suspected of containing the target nucleic acid. In some embodiments, a target is a nucleic acid having a particular non-wild-type sequence (e.g., mutant sequence (e.g., a point mutation from wild-type)) or a sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "target amplicon" is a nucleic acid generated by amplification (e.g., PCR amplification) of a target sequence. The term "sample template" refers to nucleic acid originating from a sample that is analyzed for the presence of a target. The term "target sequence" may also be used in reference to sequence information, e.g., the order of nucleotides at a site in a target nucleic acid to be detected using a sequence-specific detection assay.

The terms "control" as used herein refer to nucleic acid having known features (e.g., known sequence, known concentration, known formulation) for use in comparison to an experimental target (e.g., a nucleic acid up unknown concentration). In quantitative assays such as qPCR, QuARTS, etc., a "calibrator" or "calibration control" is a nucleic acid of known sequence, e.g., having the same sequence as a portion of an experimental target nucleic acid, and a known concentration or series of concentrations (e.g., a serially diluted control target for generation of calibration curved in quantitative PCR).

As used herein, the term "vector" refers to a nucleic acid into which a foreign nucleic acid fragment may be ligated, and that can be stably maintained and propagated in a host organism (e.g., in *E. coli* or another bacterial strain; in *S. cerevisiae*, or another fungal strain).

As used herein, the term "locus" refers to a particular position (e.g., of a mutation, polymorphism, or a C residue in a CpG dinucleotide, etc.) within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or base pair. As used herein in reference to CpG sites that may be methylated, a locus refers to the C residue in the CpG dinucleotide. As used herein in reference to a position that may be mutated (e.g., KRAS G35T, etc.), a locus refers to the nucleotide (or nucleotides) or base pair (or base pairs) that may either be in wild-type or mutant form.

As used herein, "methylation" or "methylated," as used in reference to the methylation status of a cytosine, e.g., in a CpG locus, generally refers to the presence or absence of a methyl group at position 5 of the cytosine residue (i.e., whether a particular cytosine is 5-methylcytosine). Methylation may be determined directly, e.g., as evidenced by routine methods for analysis of methylation status of cytosines, e.g., by determining the sensitivity (or lack thereof) of a particular C-residue to conversion to uracil by treatment with bisulfite. For example, a cytosine residue in a sample that is not converted to uracil when the sample is treated with bisulfite in a manner that would be expected to convert that residue if non-methylated (e.g., under conditions in which a majority or all of the non-methylated cytosines in the sample are converted to uracils) may generally be deemed "methylated."

As used herein, "sensitivity" as used in reference to a diagnostic assay, e.g., a methylation assay, refers to clinical sensitivity—the proportion of positive samples that give a positive result using a diagnostic assay. Sensitivity is generally calculated as the number of true positives identified by the assay, divided by the sum of the number of true positives and the number of false negatives determined by the assay on known positive samples. Similarly, the term "specificity" refers to the proportion or number of true negatives determined by the assay divided by the sum of the number of true negatives and the number of false positives determined by the assay on known negative sample(s).

The term "wild-type" refers to a gene, gene product, or fragment thereof that has the characteristics of that gene or gene product when isolated from a naturally occurring source and is of the sequence and/or form that is most frequently observed in a population. In contrast, the terms "modified," "mutant," and/or "variant" refer to a gene, gene product, or a fragment thereof that displays modifications in sequence and or functional properties (i.e., altered characteristics) when compared to wild-type. It is noted that naturally occurring mutants can be isolated; these are identified by the fact that they have altered characteristics when compared to the wild-type gene or gene product.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" encompasses both fragmented and combined kits.

As used herein, the term "assay system" refers to the reagents, materials, instruments, etc. for performing an assay, and the particular arrangement thereof (e.g., in a single vessel, in separate vessels, in wells of a microplate, etc.).

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc. "Methylation status information" refers to facts or data, including, but not limited to, methylation rates, methylation ratios, etc. at one or more specific loci in a subject.

As used herein, the term "colorectal cancer" includes the well-accepted medical definition that defines colorectal cancer as a medical condition characterized by cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" further includes medical conditions which are characterized by cancer of cells of the duodenum and small intestine (jejunum and ileum).

As used herein, the term "metastasis" refers to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" refers to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, "an individual is suspected of being susceptible to metastasized colorectal cancer" refers to an individual who is at an above-average risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

The term "colorectal neoplasm-specific marker" refers to any biological material that can be used to indicate the presence of a colorectal neoplasm (e.g., a premalignant colorectal neoplasm; a malignant colorectal neoplasm). Examples of colorectal neoplasm-specific markers include, but are not limited to, exfoliated epithelial markers (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA) and fecal occult blood markers (e.g., hemoglobin, alpha-defensin, calprotectin, α1-antitrypsin, albumin, MCM2, transferrin, lactoferrin, and lysozyme). For additional markers, see also U.S. Pat. Nos. 7,485,420; 7,432,050; 5,352,775; 5,648,212; U.S. RE36713; U.S. Pat. Nos. 5,527,676; 5,955,263; 6,090,566; 6,245,515; 6,677,312; 6,800,617; 7,087,583; 7,267,955; and U.S. Pat. Pub. 2012/0196756 (see, e.g., Table 1 thereof); each of which is herein incorporated by reference in their entireties.

The term "amplifying" or "amplification" in the context of nucleic acids refers to the production of multiple copies of a polynucleotide, or a portion of the polynucleotide (e.g., target), typically starting from a small amount of the polynucleotide (e.g., a single polynucleotide molecule), where the amplification products or amplicons (e.g., target amplicons) are generally detectable. Amplification of polynucleotides encompasses a variety of chemical and enzymatic processes. The generation of multiple DNA copies from one or a few copies of a target or template DNA molecule during a polymerase chain reaction (PCR; see, e.g., U.S. Pat. Nos. 4,683,195; 4,683,202; and 4,965,188; herein incorporated by reference in their entireties) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specific PCR, inverse PCR (see, e.g., Triglia, et al., (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties), and digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the term "nucleic acid detection assay" refers generally to any method of determining the nucleotide composition of all or a portion of a nucleic acid of interest. Nucleic acid detection assays include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad Sci. USA 88, 189-93 (1991)); and sandwich hybridization methods (e.g., U.S. Pat. No. 5,288,609, herein incorporated by reference in its entirety). In some embodiments, target nucleic acid is amplified (e.g., by PCR) and amplified nucleic acid is detected simultaneously using an invasive cleavage assay. Assays configured for performing a detection assay (e.g., a flap cleavage assay) in combination with an amplification assay are described in US Patent Publication US 20090253142 A1 (application Ser. No. 12/404,240), incorporated herein by reference in its entirety for all purposes. Additional amplification plus flap cleavage detection configurations, termed the QuARTS method, are described in U.S. Pat. No. 8,361,720, and U.S. patent application Ser.

No. 12/946,745; and Ser. No. 12/946,752, all incorporated herein by reference in their entireties for all purposes.

As used herein, the term "PCR reagents" refers to all reagents that are required for performing a polymerase chain reaction (PCR) on a template. As is known in the art, PCR reagents typically include a primer pair (e.g., first primer and second primer, forward primer and reverse primer, etc.), a thermostable polymerase (e.g., DNA polymerase), and nucleotides (e.g., deoxynucleoside triphosphates). Depending on the polymerase used, ions (e.g., $Mg_2^+$) may also be present (e.g., in the form of salts (e.g., $MgCl_2$). PCR reagents may optionally contain a template from which a target sequence can be amplified.

As used herein, the term "flap assay" refers to an invasive cleavage assay in which a flap oligonucleotide is cleaved in an overlap-dependent manner by a flap endonuclease to release a flap that is then detected. The principles of flap assays are well known and described in, e.g., U.S. Pat. App. No. 2013/0143216; Lyamichev et al., Nat. Biotechnol. 1999 17:292-296; Ryan et al., Mol. Diagn. 1999 4:135-44; Allawi et al., J Clin Microbiol. 2006 44: 3443-3447; herein incorporated by reference in their entireties. Certain reagents that are employed in a flap assay are described below.

The term "probe oligonucleotide" or "flap oligonucleotide" when used in reference to flap assay, refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archival thermophiles organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a "dark" quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired "flap" is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein in reference to data collected during real time PCR and PCR+ INVADER assays refer to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

DETAILED DESCRIPTION OF THE INVENTION

Real time quantitative detection assays, e.g., thermal cycling detection reactions such as real time qPCR, QuARTS assays, and qINVADER assays, typically monitor signal as a function of the number of thermal cycles. For example, one typical measure of the amount of target nucleic acid in a sample is the cycle at which signal (e.g., fluorescent signal) crosses a predetermined threshold value indicative of signal that is above background noise. Various methods have been used to calculate the threshold that is used as a determinant of signal that is above background and is thus indicative of target concentration, and the value is generally expressed as either the crossing threshold (Ct) or the crossing point (Cp). The particular signal level set as the threshold is influenced by the particular chemistry of a reaction and the instrumentation used to measure the real-time signal, and is generally set just above the baseline signal (noise) measured in early cycles, before significant target or signal amplification has occurred. In some configurations, a Ct or Cp is set as a percentage of the maximum signal, e.g., a percentage of the highest level of fluorescence measured in a calibrator or control measured during the same experiment (e.g., in a well on the same plate in a thermalcycling instrument).

Because the signal and crossing point vary from assay run to assay run, a standard curve is typically run at the same time as each experimental assay, and the quantities of the unknown samples are determined by reference to the signal curve generated from the calibration standards. The standard curve is typically from a dilution series of target nucleic acid at known concentrations, generally referred to as controls or calibrators.

The present invention provides molecules, e.g., plasmids, that find use as calibrators or reference standards for determining target nucleic acid quantities in unknown samples. In particular, provided herein are plasmids that contain multiple different target nucleic acid sequences, such that combinations of the different target nucleic acid sequences can be provided in control reactions in defined relative amounts, e.g., in equimolar amounts, for use as calibrators for quantitative detection reactions detecting the same sequences in experimental samples.

The present invention further provides methods of using the plasmids to provide mixtures having equimolar amounts of different target nucleic acids in the form of separated DNA fragments. In particular embodiments, the plasmids of the invention are configured such that a single cleavage reaction (with one or more restriction enzymes) may be used to release all of the multiple target nucleic acids from the plasmid. In preferred embodiments, each target fragment is separated by cleavage from both the plasmid vector and from all of the other target control fragments.

"Control fragments" refers to portions of nucleic acid that are to be detected or measured using the assay reaction that is to be calibrated using the plasmid. In some embodiments, a control fragment is complementary to or identical to an entire target for an assay to be calibrated by the plasmid, while in other embodiments, a control fragment comprises only a portion of a target nucleic acid to be measured using the assay calibrated using the plasmid. In some embodiments, control fragments comprise a sequence such that, upon amplification with primers for the target sequence, produce a control amplicon that is identical in sequence to the amplicon produced from the experimental target nucleic acid.

In some embodiments, a control fragment contains a sequence derived from a target nucleic acid. For example, in some embodiments, a control fragment contains a sequence representing a target nucleic acid that has been modified, e.g., treated with bisulfite in a reaction that converts unmethylated cytosine bases to uracil bases and in which methylated cytosines are not converted. Thus, in some embodiments, control fragments for use in calibrating reactions to detect bisulfite-treated target DNA contain cytosines in place of the target's methylcytosines, and thymines in place of a target's cytosines.

Calibrator plasmids of the invention are not limited to any particular number of different control fragments and may comprise, e.g., 2, 3, 4, 5, 6, 7, 8, 9, 10 . . . 15 . . . 20 . . . 50, or more different control fragments.

Although embodiments of the invention are discussed as plasmid constructs, any suitable vector may be used in embodiments of the invention. In some embodiments, the vector is a plasmid (e.g., a plasmid vector such as a pBR322, or a pUC or pGEM cloning vector plasmid), while in some embodiments, the vector is a bacteriophage vector (e.g., an M13 variant such as mp18, mp19, etc., or bacteriophage λ).

In preferred embodiments, the calibrator nucleic acid is a plasmid comprising a "vector portion" having the vector DNA, and further comprising a plurality of control fragments (e.g., in a "control portion" of the plasmid). In some embodiments, the control fragments are linked to the vector at restriction site(s) (e.g., EcoRI, SalI, etc.). In some embodiments, the control fragments are linked together at restriction sites (e.g., EcoRI, SalI, etc.). The control fragments may be contiguous (e.g., only separated by restriction sites) or may be separated by linking segments of nucleic acid (e.g., linkers including restriction sites or linkers separated from the control fragments by restriction sites). Linkers may be of any suitable length (e.g., 1-50 nucleotides, 2-40 nucleotides, 3-30 nucleotides, 4-20 nucleotides, 5-10 nucleotides, etc.).

It is contemplated that a calibrator nucleic acid according to the invention may contain more than one of either the vector portion and/or control portion. For example, in some embodiments, control fragments may be inserted into different sites in a plasmid vector, such that the vector is subdivided into non-contiguous vector portions, and the control fragments are present as non-contiguous control portions. In some embodiments, the vector portion comprises the sequence of a plasmid vector (e.g., a pUC plasmid, etc.), while the control portion comprises a plurality of different control fragments (e.g., SEQ ID NO:2, SEQ ID NO: 7, etc.) linked in series (e.g., directly or separated by linkers) and separated by restriction sites. In some embodiments, the control portion is between 150 and 3000 nucleotides in length and in certain embodiments, a control fragment is between 50 and 500 nucleotides in length (e.g., 75-200 nucleotides).

In certain embodiments, restriction sites separate the control fragments from each other. In preferred embodiments, restriction sites separate the control fragments from the vector portion. In some embodiments, restriction sites separate linker segments from the control fragments and/or the vector portion. In certain preferred embodiments, a single type of restriction site (e.g., EcoRI, SalI, etc.) separates the control fragments from each other and the vector portion of the plasmid from the control portion. In other embodiments, two or more (e.g., 2, 3, 4, 5, or more) types of restriction sites (e.g., EcoRI, SalI, etc.) separate the control fragments and/or the vector portion. In certain embodiments, multiple restriction site types separate the individual control fragments from each other and/or the control portion from the vector portion. In preferred embodiments, the types of sites are selected to allow efficient digestion of all restriction sites in a single reaction (e.g., in a single reaction vessel, concurrently, under the same conditions, etc.).

Numerous restriction site known in the art may find use in embodiments of the present invention. In some embodiments, suitable restriction sites include the recognition sites for the non-exhaustive group of restriction endonucleases consisting of AatII, AccI, Acc65I, AciI, AclI, AfeI, AflII AflIII, AgeI, AhdI, AluI, AlwI, AlwNI, ApaI, ApaLI, ApoI, AscI, AseI, AsiSI, AvaI, AvaII, AvrII, BaeI, BamHI, BanI, BanII, BbsI, BbvI, BbvCI, BceAI, BcgI, BciVI, BclI, BfaI, BfrBI, BfuAI, BglI, BglII, BlpI, Bme1580I, BmgBI, BmrI, BpmI, BsaI, BsaAI, BsaBI, BsaHI, BsaJI, BsaWI, BsaXI, BseRI, BsgI, BsiEI, BsiHKAI, BsiWI, BslI, BsmI, BsmAI, BsmBI, BsmFI, BsoBI, Bsp1286I, BspCNI, BspDI, BspEI, BspHI, BspMI, BsrI, BsrBI, BsrDI, BsrFI, BsrGI, BssHII, BssKI, BssSI, BstAPI, BstBI, BstEII, BstF5I, BstNI, BstUI, BstXI, BstYI, BstZ17I, Bsu36I, BtgI, BtrI, BtsI, Cac8I, ClaI, DdeI, DpnI, DpnII, DraI, DraII, DrdI, EaeI, EagI, EarI, EciI, EcoNI, EcoO109I, EcoRI, EcoRV, FauI, Fnu4HI, FokI, FseI, FspI, HaeII, HaeIII, HgaI, HhaI, HinP1I, HincII, HindIII, HinfI, HpaI, HpaII, HphI, Hpy99I, Hpy188I, Hpy188III, HpyCH4III, HpyCH4IV, HpyCH4V, KasI, KpnI, MboI, MboII, MfeI, MluI, MlyI, MnlI, MscI, MseI, MslI, MspI, MspAII, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PleI, PmeI, PmlI, PpuMI, PshAI, PsiI, PspGI, PspOMI, PstI, PvuI, PvuII, RsaI, RsrII, SacI, SacI, SalI, SapI, Sau96I, Sau3AI, SbfI, ScaI, ScrFI, SexAI, SfaNI, SfcI, SfiI, SfoI, SgrAI, SmaI, SmlI, SnaBI, SpeI, SphI, SspI, StuI, StyI, SwaI, TaqI, TfiI, TliI, TseI, Tsp45I, Tsp509I, TspRI, Tth111I, XbaI, XcmI, XhoI, XmaI and XmnI. In preferred embodiments, restriction sites are selected from the group of restriction sites that are not found internally in one or more of the control fragments. In particularly preferred embodiments, none of the restrictions sites used between the control fragments and between the control portion and the vector portion are found internally within any of the control fragments. In particularly preferred embodiments, separation of the control fragments from each other and the vector portion from the control portion of the plasmid is effected by cleavage with EcoRI and/or SalI restriction enzymes.

In some embodiments, the plasmids comprising multiple control fragments are used as calibration standards in assays for the identification, detection, and/or characterization of disease, a pre-disease state, response to a therapeutic action, or susceptibility to disease in a subject (e.g., human). In certain embodiments, the control fragments correspond to target sequences encompassing disease biomarkers (e.g., cancer biomarkers). In some embodiments, control fragments and target sequences each comprise at least one locus that is indicative of a disease or predisposition to a disease (e.g., cancer, such as colorectal cancer, etc.). In some embodiments, a biomarker for disease comprises a mutation (e.g., a point mutation, deletion, insertion) at a locus in a subject, while in some embodiments, a biomarker consists of a particular methylation state at a locus in a subject. In some embodiments, a biomarker is the ratio of mutated to unmutated, or methylated to unmethylated nucleic acids at a particular locus in a sample or subject. In some embodiments, a diagnostic marker is related to the quantity of a target nucleic acid present in a sample, e.g., the amount of certain DNA in a stool sample from a subject.

In certain embodiments, analysis of biomarkers comprises analysis of mutations in the KRAS gene and/or analysis of the methylation states of specific loci in BMP3 and NDRG4, and the plasmids comprise control fragments containing the corresponding loci. In preferred embodiments, the plasmids further comprise a sequence of a reference gene, e.g., beta actin (ACTB), for use, e.g., as a control for an assay (e.g., a positive control).

In particular embodiments, a calibrator plasmid for a colorectal cancer mutation biomarker assay comprises two or more control fragments corresponding to (e.g., identical to or complimentary to) target sequences encompassing loci that are indicative of cancer or pre-cancer when a particular mutation is present. An exemplary control plasmid for such an assay has the sequence of SEQ ID NO:6. Such a plasmid comprises a control portion (e.g., SEQ ID NO:7) and vector portion (e.g., pUC57). The control portion of such a plasmid comprises several (e.g., 3, 4, 5, etc.) control fragments (e.g., SEQ ID NOS. 8-10) separated by restriction endonuclease recognition sites (e.g., EcoRI). Modifications to and variations of such a plasmid are within the scope of the present invention (e.g., a vector portion comprising a different plasmid sequence or different type of vector; different restriction recognition sequences, different combinations of control fragments corresponding to difference target sequences (e.g., different cancer biomarkers), etc.

In other embodiments, a calibrator plasmid comprises target sequences encompassing loci that are indicative of cancer or pre-cancer when methylated or unmethylated. An exemplary control plasmid for such an assay has the sequence of SEQ ID NO:1. Such a plasmid comprises a control portion (e.g., SEQ ID NO:2) and vector portion (e.g., pUC57). The control portion of such a plasmid comprises several (e.g., 3, 4, 5, etc.) control fragments (e.g., SEQ ID NOS. 3-5) separated by restriction endonuclease recognition sites (e.g., EcoRI). Modifications to and variations of such a plasmid are within the scope of the present invention (e.g., a vector portion comprising a different plasmid sequence or different type of vector; different restriction recognition sequences, different combinations of control fragments corresponding to difference target sequences (e.g., different cancer biomarkers), etc.

In certain embodiments, calibrator plasmids are generated (e.g., for methylation and/or mutation assays) by inserting multiple target sequences into an existing plasmid vector (e.g., a triple insert into a pUC plasmid (e.g., pUC57, pUC19, etc.). The inserts are separated from the vector by restriction digestion sites (e.g., EcoRI and/or SalI) to allow to digestion of the plasmids (e.g., to liberate the control fragments before or after dilution to the desired concentrations.

In particular embodiments, an exemplary assay utilizing a calibrator plasmid of the present invention proceeds as follows. Nucleic acid is isolated from a biological or environmental source (e.g., stool sample). In some embodiments, the nucleic acid may be treated with a bisulfite reagent to convert non-methylated cytosines to uracils. A portion of the isolated nucleic acid is aliquoted into one or more reaction vessels (e.g., microcentrifuge tubes, wells of a microwell plate). It is not known how much of two or more target sequences are contained within the isolated nucleic acid. In an identical vessel is placed a known quantity of calibrator plasmid comprising control fragments corresponding to the target sequences of interest. The control plasmid is subjected to restriction digest with appropriate restriction endonuclease(s) to liberate the control fragments (e.g., in a single reaction). In some embodiments, each individual control fragment is liberated from the vector portion of the plasmid as well as the other control fragments. The control vessel (e.g., comprising the liberated control fragments in known quantity) and the test vessel(s) (e.g., containing the isolated nucleic acid with unknown amount of target sequence) are subject to the same reaction conditions (e.g., amplification conditions), and the results of the reactions are detected e.g., in real time, for both the target and control. The test reaction(s) are then quantified based the results of the control reaction using a known amount of starting material. In typical embodiments, the reaction is an amplification reaction, and the results that are quantified are the amount of target nucleic acid present in the sample of isolated nucleic acid.

In certain embodiments, the present invention provides reaction mixtures (reaction mix) comprising one or more calibrator plasmids described herein, or a combination of DNA fragments produced using such calibrator plasmids. Typically, these reaction mixtures contain reagents for polymerase chain reaction (PCR) amplification, although reaction mixtures for other methods of amplification and/or analysis are within the scope of the present invention. In some embodiments, reaction mixtures comprise PCR reagents for amplifying a nucleic acid target sequence. The reaction mixtures employed in the method may therefore comprise: one or more pairs of primers, a suitable PCR buffer (e.g., pH buffered, comprising salt (e.g., KCl) and a source of divalent cation (e.g., MgCl$_2$), etc.), deoxynucleoside triphosphates (e.g., dGTP, dATP, dTTP and dCTP), and a thermostable DNA polymerase. Depending on the application, the reaction mixture may also comprise additional components for further analysis, manipulation, and/or detection of polynucleotides or target sequences therein, e.g., invasive oligonucleotide(s), flap oligonucleotide(s), flap endonuclease (e.g., thermostable FEN-1), FRET cassette(s), etc.

The exact identities and concentrations of the reagents present in the reaction mixture may be similar to or the same as those employed in the field. In some embodiments, a reaction mixture contains Mg$^{2+}$ at a concentration of between about 1.8 mM and 3 mM, 4 mM to 10 mM, 6 mM to 9 mM, etc. Exemplary reaction buffers and DNA polymerases that may be employed in the subject reaction mixture include those described in various publications (e.g., Ausubel, et al., Short Protocols in Molecular Biology, 3rd ed., Wiley & Sons 1995; Sambrook et al., Molecular Cloning: A Laboratory Manual, Third Edition, 2001 Cold Spring Harbor, N.Y.; herein incorporated by reference in their entireties). Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.). Exemplary polymerases include Taq, Pfu, Pwo, UlTma and Vent, and variants thereof, although many other polymerases may be employed in certain embodiments. Exemplary flap endonucleases include Afu FEN-1, Pfu FEN-1 and Ave FEN-1 (See, e.g., WO 02/070755, and Kaiser M. W., et al. (1999) J. Biol. Chem., 274:21387).

Guidance for the reaction components suitable for use with a polymerase as well as suitable conditions for their use, is found in the literature supplied with the polymerase. Primer design is described in a variety of publications (e.g., Diffenbach and Dveksler, PCR Primer, A Laboratory Manual, Cold Spring Harbor Press 1995; R. Rapley, The Nucleic Acid Protocols Handbook (2000), Humana Press, Totowa, N.J.; Schena and Kwok et al., Nucl. Acid Res. 1990 18:999-1005; herein incorporated by reference in their entireties). Primer and probe design software programs are also commercially available, including without limitation, Primer Detective (ClonTech, Palo Alto, Calif.), Lasergene, (DNASTAR, Inc., Madison, Wis.); and Oligo software (National Biosciences, Inc., Plymouth, Minn.) and iOligo (Caesar Software, Portsmouth, N.H.).

In particular embodiments, a reaction mix contains reagents for assaying multiple different target sequences in parallel (e.g., at least 2, 3, 4 . . . 10, or more). In these cases, the reaction mix may contain multiple pairs of PCR primers. In certain embodiments, the various oligonucleotides used in the method are designed so as to not interfere with each other. In a multiplex reaction, the primers may be designed to have similar thermodynamic properties (e.g., similar $T_m$s, G/C content, hairpin stability, and in certain embodiments may all be of a similar length (e.g., from 18 to 30 nucleotides (e.g., 20 to 25 nucleotides). In some embodiments, other reagents used in the reaction mixture are $T_m$ matched, to work under the same temperature(s) as other components, or during a selected subset of temperatures used, e.g., during a thermocycling reaction.

In some embodiments, the reaction mixture is present in a vessel, including without limitation, a tube, a multi-well plate (e.g., 96-well, 384-well, 1536-well), a microfluidic device, etc. In certain embodiments, multiple multiplex reactions are performed in the same reaction vessel. Depending on how the reaction is performed, the reaction mixture may be of any volume, e.g., 0.1 µl to 5 µl, 5 µl to 200 µl (e.g., 10 µl to 100 µl), although volumes outside of this range are envisioned.

In certain embodiments, a reaction mix comprises a nucleic acid (e.g., comprising a target sequence, from a biological sample, from an environmental sample, synthetic, etc.). In particular embodiments, the mix comprises genomic DNA, fragments thereof, or an amplified version thereof (e.g., genomic DNA amplified using the methods of Lage et al, Genome Res. 2003 13: 294-307 or published patent application US20040241658 both of which are herein incorporated by reference in their entireties). In exemplary embodiments, the genomic sample may contain genomic DNA from a mammalian cell such a human, mouse, rat or monkey cell. The sample may be made from cultured cells or cells of a clinical sample (e.g., a tissue biopsy, scrape or lavage or cells of a forensic sample (i.e., cells of a sample collected at a crime scene), etc.).

In particular embodiments, a nucleic acid in a reaction mix is obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject (e.g., a human) and it may be processed prior to use in the subject assay. For example, the nucleic acid may be extracted from the sample prior to use, methods for which are known. In some embodiments, nucleic acid is extracted, isolated, purified, removed from stool (e.g., human stool, a stool sample, etc.). For example, nucleic acid (e.g., DNA) can be extracted from stool from any number of different methods, including those described in, e.g., Coll et al. J. of Clinical Microbiology 1989 27: 2245-2248; Sidransky et al. Science 1992 256: 102-105; Villa, Gastroenterology 1996 110: 1346-1353; Nollau, BioTechniques 1996 20: 784-788; U.S. Pat. Nos. 5,463,782; 7,005,266; 6,303,304; 5,741,650; herein incorporated by reference in their entireties. Commercial DNA extraction kits for the extraction of DNA from stool include the QIAamp stool mini kit (QIAGEN, Haden, Germany), Instagene Matrix (Bio-Rad, Hercules, Calif.), and RapidPrep Micro Genomic DNA isolation kit (Pharmacia Biotech Inc., Piscataway, N.J.), among others. In preferred embodiments, DNA is extracted from stool samples as described, e.g., in U.S. Patent Publication 2012/0288868, incorporated herein by reference in its entirety for all purposes. In some embodiments the DNA is treated with bisulfite prior to use in an assay, wherein unmethylated cytosine bases are converted to uracil bases.

In certain embodiments, a reaction mixture (e.g., comprising a calibrator plasmid) comprises one or more reagents (e.g., oligonucleotides such as primers, flap probes, detection cassettes; enzymes such as polymerases; chemical reagents; etc.) for performing amplification, processing, manipulation, analysis, detection steps or assays (e.g., other than and/or in addition to PCR). The present invention is not limited by the scope of the nucleic acid analysis manipulation, and/or detection methods with which it finds use.

In certain embodiments, a reaction mixture (e.g., comprising a calibrator plasmid and optionally additional reagents (e.g., PCR reagents, detection reagents, etc.)) comprises one or more restriction endonucleases. In some embodiments, the restriction endonuclease or restriction endonucleases are appropriately selected to cleave the calibrator plasmid at restriction sites between the individual control fragments and/or between the control portion and the vector portion. In some embodiments, a reaction mix comprises a single restriction endonuclease (e.g., one endonuclease capable of cleaving the restriction sites between the individual control fragments and between the control portion and the vector portion). In some embodiments, a reaction mix comprises two or more (e.g., 2, 3, 4, 5, 6, 7, or more) restriction endonucleases (e.g., all the endonucleases required for cleaving the restriction sites between the individual control fragments and between the control portion and the vector portion). In certain embodiments in which a reaction mix comprises more than one restriction endonuclease, all of the endonucleases in the mix are active (e.g., actively cleave their corresponding recognition site) in the same reaction conditions (e.g., buffer, pH, salt concentration, temperature, etc.). In some embodiments, suitable restriction enzymes for inclusion in a reaction mix are selected from, for example, the non-exhaustive group consisting of AatII, AccI, Acc65I, AciI, AcII, AfeI, AflIII AflIIII, AgeI, AhdI, AluI, AlwI, AlwNI, ApaI, ApaLI, ApoI, AscI, AseI, AsiSI, AvaI, AvaII, AvrII, BaeI, BamHI, BanI, BanII, BbsI, BbvI, BbvCI, BceAI, BcgI, BciVI, BclI, BfaI, BfrBI, BfuAI, BglI, BglII, BlpI, Bme1580I, BmgBI, BmrI, BpmI, BsaI, BsaAI, BsaBI, BsaHI, BsaJI, BsaWI, BsaXI, BseRI, BsgI, BsiEI, BsiHKAI, BsiWI, BsII, BsmI, BsmAI, BsmBI, BsmFI, BsoBI, Bsp1286I, BspCNI, BspDI, BspEI, BspHI, BspMI, BsrI, BsrBI, BsrDI, BsrFI, BsrGI, BssHII, BssKI, BssSI, BstAPI, BstBI, BstEII, BstF5I, BstNI, BstUI, BstXI, BstYI, BstZ17I, Bsu36I, BtgI, BtrI, BtsI, Cac8I, ClaI, DdeI, DpnI, DpnII, DraI, DraII, DrdI, EaeI, EagI, EarI, EciI, EcoNI, EcoO109I, EcoRI, EcoRV, FauI, Fnu4HI, FokI, FseI, FspI, HaeII, HaeIII, HgaI, HhaI, HinP1I, HincII, HindIII, HinfI, HpaI, HpaII, HphI, Hpy99I, Hpy188I, Hpy188III, HpyCH4III, HpyCH4IV, HpyCH4V, KasI, KpnI, MboI, MboII, MfeI, MluI, MlyI, MnlI, MscI, MseI, MsII, MspI, MspAII, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PleI, PmeI, PmlI, PpuMI, PshAI, PsiI, PspGI, PspOMI, PstI, PvuI, PvuII, RsaI, RsrII, SacI, SacI, SalI, SapI, Sau96I, Sau3AI, SbfI, ScaI, ScrFI, SexAI, SfaNI, SfcI, SfiI, SfoI, SgrAI, SmaI, SmlI, SnaBI, SpeI, SphI, SspI, StuI, StyI, SwaI, TaqI, TfiI, TliI, TseI, Tsp45I, Tsp509I, TspRI, Tth111I, XbaI, XcmI, XhoI, XmaI and XmnI. In some embodiments, a reaction mixture comprises EcoRI and/or SalI.

In some embodiments, multiple different reaction mixes (e.g., at least one comprising a calibrator plasmid and at least one comprising a target sequence) are provided (e.g., for use in an experiment or assay. In some embodiments, multiple vessels (e.g., wells, tubes, channels, etc.) are provided, each containing a reaction mix (e.g., at least one comprising a calibrator plasmid and at least one comprising an experimental target nucleic acid).

In certain embodiments, the plasmid compositions, reaction mixtures, and/or methods described herein find use in a variety of diagnostic, medical, analytical, and research applications, and the invention should not be viewed as limited to any particular field or use. However, in particular embodiments, the present invention finds use in the analysis, detection, characterization, etc. of nucleic acid (e.g., human nucleic acid, target nucleic acid, etc.) from stool. Compositions, methods, devices, etc. for use the embodiments described herein are found in, for example, U.S. Pat. Nos. 8,361,720; 7,981,612; 7,368,233; 6,964,846; 6,919,174; 6,849,403; 6,844,155; 6,818,404; 6,750,020; 6,586,177; 6,551,777; 6,503,718; 6,498,012; 6,482,595; 6,475,738; 6,428,964; 6,415,455; 6,406,857; 6,351,857; 6,303,304; 6,300,077; 6,280,947; 6,268,136; 6,203,993; 6,146,828; 6,143,529; 6,020,137; 5,952,178; 5,928,870; 5,888,778; 5,830,665; 5,741,650; 5,670,325; each of which is herein incorporated by reference in its entirety for any purpose. In certain embodiments, the compositions and methods described herein find use in, for example, a quantitative allele-specific real-time target and signal amplification (QuARTS) assay, such as the ones described in Lou et al. Clinical Chemistry, February 2012 vol. 58 no. 2 375-383; herein incorporated by reference in its entirety.

In some embodiments, compositions and methods are employed in calibrated assays to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which mutation may be associated with breast cancer, melanoma, renal cancer, endometrial cancer, ovarian cancer, pancreatic cancer, leukemia, colorectal cancer, prostate cancer, mesothelioma, glioma, meullobastoma, polythemia, lymphoma, sarcoma or multiple myeloma (see, e.g., Chial 2008 Proto-oncogenes to oncogenes to cancer. Nature Education 1:1).

EXPERIMENTAL

Experiments were conducted during development of embodiments of the present invention to develop an assay to detect and quantify nucleic acid having mutations in the KRAS gene and methylated C's in the BMP3 and NDRG4 genes. The quantification of the amount of mutated or methylated copies of these genes present in a sample is based on the comparison of the assay signal to a standard curve generated using known concentrations of the DNA calibrator fragments designed to mimic the targeted DNA captured from stool samples.

Plasmids were constructed containing the targeted DNA sequences as control fragments, and the plasmids were transformed into an appropriate *E. coli* host for propagation and for maintenance as glycerol stocks.

Design of Calibrator Plasmids

To most closely mimic the target nucleic acids captured from stool samples, the sequence of each of the control fragments was designed to contain the entire captured sequence, as opposed to just the amplified region. This captured sequence includes the region containing the mutated/methylated bases (e.g., for detection (e.g., by INVADER invasive cleavage assay), flanking regions containing primer binding sequences (e.g., for amplification), and the capture region (e.g., containing a sequence targeted by capture probes used to selectively purify these DNAs from patient stool).

Plasmids were generated with three different control fragments each. Insertion of multiple control fragments into a single plasmid vector simplified and streamlined the calibrator manufacturing process, and ensures that all control fragments are at an equimolar ratio. Each of the triplex plasmids can therefore be used to generate three standard curves, one for each control fragment present in the construct.

EcoRI sites are present in between each control fragment and at the ends of the entire triplex insert. Complete liberation of the three inserts is accomplished by incubation with the restriction enzyme EcoRI under appropriate conditions. The resulting liberated fragments more closely mimic the size of the DNA molecules captured from stool samples than does linearized plasmid.

TABLE 1

Restriction Fragments sizes for digested calibrator plasmids

| fragment | EcoRI site | size (bp) |
|---|---|---|
| kras 3141 bp, EcoRI digest fragments | | |
| pUC 57 vector | 858(-3141-) 397-433 | 2680 + 36 |
| KRAS 35A | 433-553 | 160 |
| KRAS 35C | 593-753 | 160 |
| ACTB | 753-858 | 105 |
| A NB 299 2 bp, EcoRI digest fragments | | |
| pUC 57 vector | 706(-2992-) 397-436 | 2683 + 39 |
| BMP3 | 436-509 | 73 |
| NDRG4 | 509-603 | 94 |
| ACTB | 603-706 | 103 |

Equivalency Between Thymine and Deoxyuracil in a Calibrator DNA

As discussed above, in methylation assays a target DNA is first treated with a bisulfite reagent that converts unmethylated cytosines to uracils. Upon amplification, the uracils are read by a polymerase as thymines and the methyl Cs are read as cytosines, such that the final amplification product contains cytosines where each methyl C appeared in the target, and thymines where each non-methyl C appeared. In making a calibrator designed to mimic bisulfite converted target DNA, it was determined that the presence of deoxyuracils in target DNA did not have any impact on the efficiency of amplification in the early cycles (i.e., cycles in which the original target make a significant contribution to the reaction). Thus, the calibrators were produced using cytosine in place of methyl cytosine and thymine in place of uracil.

Methylation Calibrator Plasmid Design

A calibrator plasmid was designed and manufactured to contain control fragments for ACTB, NDRG4, and BMP-3 (ANB calibrator). The methylation assay quantifies the amount of methylated NDRG4 sequence (reporting to dye 1), the amount of methylated BMP3 sequence (reporting to dye 2), and the amount of wild type ACTB sequence (reporting to dye 3) in a patient stool sample. As discussed above, the assay uses selective bisulfite conversion of non-methylated cytosines to uracil and non-conversion of methylated cytosines. The control plasmid was constructed using the "converted" version of the NDRG4, BMP3, and ACTB sequences. The structure of this embodiment of the methylation calibrator plasmid is shown in FIG. 1.

Mutation Calibrator Plasmid Design

A KRAS mutation calibrator plasmid (KRAS calibrator) was also designed and manufactured with multiplexed control fragments. The KRAS mutation control plasmid contains both the KRAS 38A (reporting to dye 1) and the KRAS 35C (reporting to dye 2) mutations, and the wild type beta actin (reporting to dye 3). The structure of this embodiment of the mutation calibrator plasmid is shown in FIG. 2.

Production and Manufacturing of Calibrator Plasmids

Calibrator plasmids were produced by Genscript (GenScript USA Inc. 860 Centennial Ave. Piscataway, N.J. 08854, USA), IDT (Integrated DNA Technologies, Inc., 6868 Nancy Ridge Drive, San Diego, Calif. 92121 USA), and/or Aldevron (3233 15th Street South, Fargo, N. Dak., 58104 USA), according to the designs shown herein (see FIGS. 1 and 2).

Concentrations of the plasmid preparations were determined by measuring absorption at 260 nm ($A_{260}$). Plasmids were digested with EcoRI restriction enzyme and used in QuARTS or other detection assays to assess functionality and consistency (e.g., concentration, curve shape, fluorescence maxima and minima). Digested calibrator plasmids were purified as described below.

Purification of Calibrator Plasmids

A preparation of the ANB calibrator was produced and purified over an anion exchange column (preparation "32233F"). A portion of the plasmid was then further purified using a hydrophobic interaction column (preparation "32233G"). The two preparations were cut with EcoRI, purified, and serial dilutions of each purified preparation from 1E7 to 1E0 copies were made. Each of the three target sequences (ACTB, BMP3, and NDRG4) was detected using triplex QuARTs assays (FIG. 3). These data show that the purification methods were functionally equivalent.

Dilution of Calibrator Plasmids

The calibrators were formulated at an appropriate concentration for use in target detection assays, and were suspended in the same buffer that is used for eluting experimental DNA in the final (post-bisulfite) nucleic acid purification step (e.g., 10 mM Tris-HCl, pH 8 and 0.1 mM EDTA, or 10 mM Tris-HCl, pH 8, 0.1 mM EDTA, and 20 ng/µL yeast tRNA), to ensure that the calibrators and samples are in the same buffer going into the detection reaction.

The effect of the diluent used for making serial dilutions of the plasmid calibrators was evaluated by comparing 10 mM Tris-HCl, pH 8 and 0.1 mM EDTA to 10 mM Tris-HCl, pH 8, 0.1 mM EDTA, and 20 ng/µL yeast tRNA. Results showed equivalent performance between the two diluents tested (see Table 2).

TABLE 2

Effect of dilution buffer on calibrator quantification.

Calibrators diluted in 10 mM Tris, 0.1 mM EDTA

| Strands in Reaction | NDRG4 Strands | Standard Deviation NDRG4 Strands | BMP3 Strands | Standard Deviation BMP3 Strands | ACTB Strands | Standard Deviation ACTB Strands |
|---|---|---|---|---|---|---|
| 200,000 | 225,566 | 21,051 | 205,231 | 9,238 | 185,070 | 971 |
| 20,000 | 21,600 | 240 | 19,795 | 236 | 16,367 | 648 |
| 2,000 | 1,880 | 37 | 1,862 | 42 | 1,449 | 87 |
| 200 | 169 | 7 | 178 | 42 | 128 | 14 |
| 20 | 21 | 1 | 19 | 3 | 10 | 0 |

Calibrators diluted in 10 mM Tris, 0.1 mM EDTA, 20 ng/µl tRNA

| Strands in Reaction | NDRG4 Strands | Standard Deviation NDRG4 Strands | BMP3 Strands | Standard Deviation BMP3 Strands | ACTB Strands | Standard Deviation ACTB Strands |
|---|---|---|---|---|---|---|
| 200,000 | 187,292 | 8,602 | 184,520 | 12,288 | 224,485 | 986 |
| 20,000 | 19,893 | 525 | 20,246 | 1,112 | 18,043 | 184 |
| 2,000 | 2,186 | 100 | 2,170 | 52 | 1,799 | 3 |
| 200 | 217 | 20 | 224 | 44 | 208 | 23 |
| 20 | 18 | 0 | 18 | 3 | 21 | 1 |

Quantitation of Calibrators

Calibrator plasmids are used to generate the standard curves by which experimental samples, e.g., patient samples, are quantified. Thus, assessing the absolute number of target copies in the calibrator reagent is of importance.

In order to ensure accurate determination of the number of detectable copies present, Poisson sampling theory was employed. By testing a large number of replicates containing on average 1 copy/replicate and determining the actual number of positive events, the actual number of copies present in the original sample can be determined (see, e.g., Design and analysis of serial limiting dilution assays with small sample sizes, J Immunol Methods. 1999 January 1; 222(1-2):13-29; herein incorporated by reference in its entirety). In practice, this is done by diluting the calibrator plasmid down to an expected concentration of 1 copy/well and running QuARTS assays on the target in each well of 384 well plate. The "percent positive wells" is used to back calculate the input concentration (See Table 3). According to Poisson sampling theory, diluting the 32233F ANB triplex calibrator to an expected concentration of 0.1 and 1.0 copies/reaction and running an entire 384 well assay plate at each concentration and counting the number of positive wells should result in 9% and 63% positivity, respectively.

TABLE 3

Poisson verification of the 32233F ANB triplex calibrator concentration:
EXPECTED 0.1 COPY/WELL

| | NDRG4 | BMP3 | ACTB |
|---|---|---|---|
| # POSITIVE WELLS | 30 | 43 | 39 |
| % POSITIVE WELLS | 0.078125 | 0.111979 | 0.101563 |
| CALCULATED COPIES/WELL | 0.0814 | 0.119 | 0.107 |
| % OF EXPECTED | 81% | 119% | 107% |
| # POSITIVE WELLS | 241 | 230 | 225 |
| % POSITIVE WELLS | 0.627604 | 0.598958 | 0.585938 |
| CALCULATED COPIES/WELL | 0.99 | 0.91 | 0.88 |

TABLE 3-continued

Poisson verification of the 32233F ANB triplex calibrator concentration:
EXPECTED 0.1 COPY/WELL

| | NDRG4 | BMP3 | ACTB |
|---|---|---|---|
| % OF EXPECTED | 99% | 91% | 88% |
| AVG % OF EXPECTED 98% | | | |

Effect of Purification Methods on Concentration Measurement by UV Absorbance

While ultraviolet absorbance at 260 nm wavelength ($A_{260}$) is a direct and is generally an accurate method for DNA quantitation, the accuracy can be affected by the purification method, DNA purity, sequence, length, solution matrix, single vs. double strandedness and other factors that may vary between different DNA preparations. Such variation is observed when small scale plasmid preparations (e.g., that do not include an anion exchange step) are compared to larger scale preparations that include an anion exchange step as part of the purification procedure. FIG. 5 compares the $A_{260}$ measurement for the Poisson-verified concentration of the 32233 F calibrator, as discussed above, to the $A_{260}$ determinations from plasmids prepared by several different methods. These data show that the $A_{260}$ method of determining DNA concentration was substantially more accurate when the DNA was prepared by a method comprising an anion exchange step. Use of the midi-scale plasmid prep with the Q-tip 20 AX purification step gave measurements that correlated well with the concentrations determined using the Poisson sampling method described above.

Comparison of Individual, Biplex, and Triplex Calibration Controls

The target sequences were evaluated as individual constructs, biplexed with the beta actin control sequence in the same plasmid vector, and triplexed in the same plasmid vector, as discussed above. The different types of constructs were tested to determine whether the triplexed calibrators would give equivalent result compared to either individual constructs, or constructs with a test sequence biplexed in a plasmid with the beta-actin control. The target sequences in the plasmid constructs were digested to release them from the plasmid vector prior to testing, as discussed above

TABLE 4

QuARTS mutation assay dilution series of triplex calibrator alongside the individual mutations biplexed with the ACTB control.

| SampleID | Strands/well | FAM strands (38A, 34T, 35T) | HEX strands (35A, 35C, 34A, 34C) | Quasar strands (ACTB) | | x-reactivity vs wild type | |
|---|---|---|---|---|---|---|---|
| 35C/38A/ACTB triplex std | 2,000,000 | 2,037,641 | 1,657,527 | 1,854,666 | | | |
| 35C/38A/ACTB triplex std | 200,000 | 201,989 | 196,152 | 202,580 | | | |
| 35C/38A/ACTB triplex std | 20,000 | 20,216 | 19,238 | 19,429 | | | |
| 35C/38A/ACTB triplex std | 2,000 | 1,972 | 2,079 | 1,953 | | | |
| 35C/38A/ACTB triplex std | 200 | 188 | 221 | 213 | | | |
| 35C/38A/ACTB triplex std | 20 | 22 | 19 | 20 | | | |
| 35C/38A/ACTB triplex std | 2 | 1 | 5 | 3 | | | |
| 35C/ACTB biplex std | 2,000,000 | | 1,477,979 | 1,447,067 | | | |
| 35C/ACTB biplex std | 200,000 | | 166,331 | 149,833 | | | |
| 35C/ACTB biplex std | 20,000 | | 17,453 | 15,480 | | | |
| 35C/ACTB biplex std | 2,000 | | 1,898 | 1,484 | | | |
| 35C/ACTB biplex std | 200 | | 184 | 133 | | | |
| 35C/ACTB biplex std | 20 | | 20 | 18 | | | |
| 35C/ACTB biplex std | 2 | | 4 | — | | | |
| 38A/ACTB biplex std | 2,000,000 | 2,107,306 | | 1,765,748 | | | |
| 38A/ACTB biplex std | 200,000 | 199,158 | | 192,635 | | | |
| 38A/ACTB biplex std | 20,000 | 20,891 | | 18,966 | | | |
| 38A/ACTB biplex std | 2,000 | 1,940 | | 1,834 | | | |
| 38A/ACTB biplex std | 200 | 168 | | 178 | | | |
| 38A/ACTB biplex std | 20 | 13 | | 9 | | | |
| 38A/ACTB biplex std | 2 | 5 | | — | | | |
| wild type | 200,000 | 30 | 82 | — | | 0.015% | 0.041% |
| wild type | 100,000 | 14 | 37 | — | | 0.014% | 0.037% |
| wild type | 20,000 | 4 | 5 | — | | 0.021% | 0.026% |
| wild type | 2,000 | 0 | 0 | — | | 0.008% | 0.016% |
| | | | | Avg x-reativity vs wt target | | 0.014% | 0.030% |

These data show that the triplex construct produces results equivalent to detection of each individual target, or detection of each target biplexed with the beta actin control, demonstrating equivalency and shows the low cross-reactivity of the detection assays with wild type sequences.

Experiments conducted during development of embodiments of the present invention demonstrate the successful generation of calibrator plasmids for the quantification of target sequences in a sample. In particular, plasmid calibrators were designed, manufactured, and tested for use as methylation and mutation assay calibrators for use in the QuARTS assays.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, biology, chemistry, biochemistry, medical sciences, or related fields are intended to be within the scope of the following claims.

The invention claimed is:

1. A calibrator DNA comprising:
   (a) a vector portion, and
   (b) a control portion;
   wherein the control portion comprises three or more linked control fragments separated by restriction endonuclease recognition sites, wherein each of said three or more control fragments comprises a sequence corresponding to a portion of a human gene, or comprises a sequence corresponding to a portion of a human gene in which residues corresponding to non-methylated C residues in that human gene are replaced with T residues, and wherein residues corresponding to methylated C residues in the human gene are replaced with C residues,
   wherein the three or more control fragments comprise sequences corresponding to portions of the human ACTB, NDRG4, and BMP3 genes, wherein residues corresponding to non-methylated C residues in the human ACTB, NDRG4, and/or BMP3 genes are replaced with T residues, and wherein residues corresponding to methylated C residues in the human ACTB, NDRG4, and BMP3 genes are replaced with C residues,
   wherein the vector portion circularizes the calibrator DNA by flanking both ends of the control portion, and wherein the vector portion and the control portion are separated by restriction endonuclease recognition sites; and wherein the restriction endonuclease recognition sites that separate the vector portion from the control portion, and each of the linked control fragments from each other are recognition sites for the same restriction endonuclease.

2. The calibrator DNA of claim 1, wherein the control portion is between 50 and 2000 nucleotides in length.

3. The calibrator DNA of claim 2, wherein the control portion is between 200 and 600 nucleotides in length.

4. The calibrator DNA of claim 1, wherein each control fragment is between 10 and 500 nucleotides in length.

5. The calibrator DNA of claim 4, wherein each control fragment is between 50 and 200 nucleotides in length.

6. The calibrator DNA of claim 1, wherein the control portion further comprises one or more of the control fragments comprising a sequence corresponding to a portion of the human KRAS gene.

7. The calibrator DNA of claim 6, wherein one control fragment comprises a sequence corresponding to a portion of the human KRAS gene having a 38A mutation.

8. The calibrator DNA of claim 6, wherein one control fragment comprises a sequence corresponding to a portion of the human KRAS gene having a 35C. mutation.

* * * * *

UNITED STATES PATENT AND TRADEMARK OFFICE
CERTIFICATE OF CORRECTION

PATENT NO.        : 10,253,358 B2
APPLICATION NO.   : 15/033803
DATED             : April 9, 2019
INVENTOR(S)       : Michael J. Domanico et al.

It is certified that error appears in the above-identified patent and that said Letters Patent is hereby corrected as shown below:

In the Claims

Column 32, Claim 8 Line 57 should read:
of the human KRAS gene having a 35C mutation.

Signed and Sealed this
Twenty-fifth Day of June, 2019

Andrei Iancu
*Director of the United States Patent and Trademark Office*